(12) United States Patent
Miller et al.

(10) Patent No.: US 6,649,774 B2
(45) Date of Patent: Nov. 18, 2003

(54) CATALYSTS AND PROCESSES FOR THE CONVERSION OF SUCCINATES TO CITRACONATES OR ITACONATES

(75) Inventors: Dennis J. Miller, West Richland, WA (US); Dushyant Shekhawat, East Lansing, MI (US); Kirthivasan Nagarajan, Watervliet, NY (US); James E. Jackson, Haslett, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 10/226,474

(22) Filed: Aug. 23, 2002

(65) Prior Publication Data

US 2003/0120110 A1 Jun. 26, 2003

Related U.S. Application Data

(62) Division of application No. 09/667,842, filed on Sep. 21, 2000, now Pat. No. 6,504,055.
(60) Provisional application No. 60/208,668, filed on Jun. 1, 2000.

(51) Int. Cl.$^7$ .............................................. C07D 307/34
(52) U.S. Cl. ....................................................... 549/261
(58) Field of Search ......................................... 549/261

(56) References Cited

U.S. PATENT DOCUMENTS

| | | |
|---|---|---|
| 3,835,162 A | 9/1974 | Tate et al. |
| 3,960,901 A | 6/1976 | Berg |
| 3,987,107 A | 10/1976 | McClellan et al. |
| 4,016,106 A | 4/1977 | Sawyer et al. |
| 4,235,756 A | 11/1980 | Slaugh |
| 4,301,033 A | 11/1981 | Takumi et al. |
| 4,420,641 A | 12/1983 | Gerberich et al. |
| 4,450,301 A | 5/1984 | McMillan et al. |
| 4,967,014 A | 10/1990 | Masamoto et al. |
| 5,032,379 A | 7/1991 | Pedersen |
| 5,166,121 A | 11/1992 | Khare et al. |
| 6,015,485 A | 1/2000 | Shukis et al. |

FOREIGN PATENT DOCUMENTS

| | | |
|---|---|---|
| JP | 49101326 | 9/1974 |
| JP | 49101327 | 9/1974 |

OTHER PUBLICATIONS

Sakai, Bull. Chem. Soc. Japan 49 219 (1976).

Corma, A., et al., J. Catal. 148 205–212 (1994).

Rebenstorf, B., et al., J. Catal. 128 293–302 (1991).

*Primary Examiner*—Paul J. Killos
(74) *Attorney, Agent, or Firm*—Ian C. McLeod

(57) ABSTRACT

Processes for producing citraconic anhydride and citraconic acid using porous materials with specific surface acidities and surface areas are described. The preferred catalyst is a porous gamma alumina. Itaconic acid is produced from citraconic acid. Itaconic acid is an intermediate to a variety of compounds including polymers.

7 Claims, 10 Drawing Sheets

CATALYSTS AND PROCESSES FOR THE CONVERSION OF SUCCINATES TO CITRACONATES OR ITACONATES

CROSS REFERENCE TO RELATED APPLICATIONS

This application is a divisional of copending application (s) application No. 09/667,842 filed on Sep. 21, 2000 U.S. Pat. No. 6,504,055.

BACKGROUND OF THE INVENTION (1) Field of the Invention

This invention comprises catalysts and a process to manufacture itaconic acid via condensation of succinic acid or its esters and formaldehyde. Components of the invention include the catalysts, which facilitate the condensation to form the intermediate citraconic anhydride, and the subsequent process steps for separation of citraconic anhydride from unreacted succinate, and conversion of citraconate to itaconate. The process facilitates the use of a number of formaldehyde and succinate substrates, and produces higher selectivity toward the desired products at lower cost than the prior art. Itaconic acid is a valuable monomer in the formulation of polymers because of its unique chemical properties, which derive primarily from the conjugation of its two carboxyl groups and its methylene group. The methylene group is able to take part in addition polymerization giving polymers with many free carboxyl groups that confer advantageous properties on the resulting polymer.

(2) Description of Related Art

Itaconic acid is currently produced commercially by the fermentation of glucose using *Aspergillus Terreus*. This fungal fermentation is carried out in batch processes, which require 8–10 days per batch. The fermentation requires dilute solutions (~10 wt % glucose as a feed) and itaconate yields are on the order of 50–60% of theoretical. The current world market for itaconic acid is approximately 20 million lb/yr at a selling price of $2.00/lb. The only U.S. manufacturer at present is Cargill (Minneapolis, Minn.).

The catalytic route to itaconic acid has several distinct advantages over the current commercial fungal fermentation route. First, the rate of the catalytic reaction is several orders of magnitude faster than the biological reaction, so that the reactor vessel is smaller than the fermenter. Second, the difficulties involved with the fungal fermentation (product inhibition, sensitivity of microorganisms to process changes, etc.) are avoided. Third, separation and recovery costs should be lower via the catalytic route, so the expected production cost of itaconic acid is substantially lower than via fermentation.

There exist several patents in the literature which describe catalytic routes to citraconate or itaconate from succinates. U.S. Pat. No. 3,835,162 (Tate and Berg, assigned to Pfizer, Inc., 1974) describes catalysts and process conditions for reactions of succinic anhydride or succinate esters and formaldehyde (as trioxane or gaseous formaldehyde, in 3 to 5-fold excess) to citraconic anhydride. Yields as high as 70% were obtained for short periods of time in a microreactor consisting of a gas chromatography column packed with catalyst. The catalyst consisted of salts (thorium sulfate, potassium hydrogen phosphate, lithium phosphate, and others) supported on a lower surface area alumina (30–40 $m^2/g$); catalyst deactivation was observed at extended reaction times. A crude method for recovery of itaconate was described.

Another prior process for producing itaconate from succinate is described in two Japanese patents (JP 49101326 and JP 49101327, Shimizui and Fujii, assigned to Denki Kagaku Kogyo K. K., 1974). Silica-alumina compounds, including zeolitic materials, both with and without the addition of salts such as copper chloride, zinc chloride, or lanthanum chloride, were used as catalysts. In all studies, formaldehyde (as Formalin or trioxane) was used as the limiting reagent. Yields of citraconate plus itaconate up to 75% of theoretical based on formaldehyde were obtained, but yields based on succinate fed were no greater than 32%. These patents gave no information regarding a process for the conversion to itaconate, and there is no mention of the problem of catalyst deactivation or recycling of the succinate stream.

Sakai (Bull. Chem. Soc. Japan 49 219 (1976)) has further investigated the isomerization of citraconic acid to itaconic acid, and achieved yields of 65% itaconic acid. Sakai makes no mention of a recycle step or the reisomerization of byproducts back to citraconic acid. The conversion of citramalic acid, one of the byproducts of citraconic acid isomerization, back to citraconic acid has been reported by Berg (U.S. Pat. No. 3,960,901 to Pfizer (1976)).

SUMMARY OF THE INVENTION

The present invention relates to a process for the preparation of citraconic anhydride which comprises: contacting a molar excess of an aqueous solution of formaldehyde, gaseous formaldehyde or trioxane in a solvent with at least one compound from the group consisting of succinic anhydride and di-lower alkyl esters of succinic acid in vapor phase at a temperature from about 320° to 440° C., at a pressure from about 20 to 400 psi, at a Weight Hourly Space Velocity (WHSV) from about 0.3 to 4 kg succinate/hr*kg catalyst in the presence of a catalyst consisting of a porous material having a surface area between about 30 $m^2/g$ and 700 $m^2/g$, surface acid site density from about 66 to 2350 micromole/g, surface base site density from about 0 to 500 micromole/g and acid strength ($pK_a$) of about +3 to −3 until reaction is substantially complete and recovering from the reaction products the citraconic anhydride thereby produced, said lower alkyl having from 1 to 4 carbon atoms. The citraconic anhydride is hydrolyzed and isomerized to itaconic acid in an aqueous solution.

The present invention particularly relates to a process for the preparation of itaconic acid from citraconic acid which comprises:

(a) isomerizing citraconic acid to itaconic acid in an aqueous solution at a first temperature of about 140° C. to 200° C., which produces citramalic acid and mesaconic acid as by-products;

(b) crystallizing and separating the itaconic acid from the aqueous solution by cooling to a temperature between about 20° to 25° C.; and (c) heating the aqueous solution from step (b) to a temperature of 200° to 300° C. in the presence of a catalyst to convert any of the itaconic acid remaining in the aqueous solution and the by-products in the aqueous solution to citraconic acid;

(d) recycling the citraconic acid solution of step (c) to step (a).

The present invention is superior to that of the Pfizer patent (U.S. Pat. No. 3,835,162) in several ways. First, it requires only a metal oxide such as alumina in order to obtain good yields. This catalyst is more stable than the salt-impregnated alumina described in the Pfizer patent, especially during the catalyst regeneration step (an integral part of the process). Second, it has been demonstrated that Formalin™ (37% formaldehyde in water) and Formcel™ (55% formaldehyde in methanol/water) can be used instead of trioxane or gaseous formaldehyde. Both of these alternate formaldehyde sources are readily available commercially, whereas trioxane or gaseous formaldehyde are not. Third, the present invention includes an improved process for forming and purifying itaconic acid. Finally, it is has been demonstrated by this invention that a continuous flow reaction system is much closer to a commercially viable process concept than the micro-reactor system used in the Pfizer patent.

The present invention provides a more complete process for converting succinate to itaconate than the Japanese patents, including a succinate recycle step, catalyst regeneration, and recovery and purification of itaconic acid. Formcel is a viable formaldehyde source in addition to Formalin. The porous material catalyst is generally aluminum based and has particular characteristics as defined above. It has a mildly acidic and basic surface.

The present invention also relates to a process for the preparation of formaldehyde, citraconic acid and succinic acid which comprises:

(a) reacting a molar excess of formaldehyde with dimethyl succinate in vapor phase with a catalyst, the catalyst consisting of a porous material having a surface area between about 30 m$^2$/g and 700 m$^2$/g, surface acid site density from about 66 to 2350 micromole/g, surface base site density from about 0 to 500 micromole/g and acid strength (pKa) of about +3 to –3 until reaction is substantially complete and recovering from the reaction products the citraconic anhydride thereby produced, said lower alkyl having from 1 to 4 carbon atoms at a temperature of 320° to 440° C. at a pressure of about 20 to 400 psi;

(b) hydrolyzing the citraconic anhydride to citraconic acid and the dimethyl succinate to succinic acid at elevated temperatures in water so that the methanol is distilled from the reaction mixture;

(c) oxidizing the methanol from step (b) to produce formaldehyde; and (d) separating the citraconic acid and succinic acid from the reaction mixture.

In summary, the present invention is a new route for itaconic acid formation from succinates. It encompasses a complete process for the conversion which includes catalysts and reaction conditions for efficient conversion.

DESCRIPTION OF PREFERRED EMBODIMENTS

The present invention uses preferred alumina based solid particles which are substantially free of other metals. The particles are calcined and have an acid strength pK$_a$ between about –3 and 3 and a surface area of at least about 100 m$^2$/g. Included in the preferred materials are gamma alumina and calcined aluminum phosphate. Gamma alumina is described in U.S. Pat. No. 6,015,485 to Shukis et al; U.S. Pat. No. 5,166,121 to Khare et al; U.S. Pat. No. 5,032,379 to Pedersen; U.S. Pat. No. 4,301,033 to Takumi et al; U.S. Pat. No. 4,235,756 to Slauqh; U.S. Pat. No. 4016,106 to Sawyer et al; U.S. Pat. No. 3,835,162 to Tate et al.

DESCRIPTION OF PREFERRED EMBODIMENTS

Feed Materials

Figure 1:
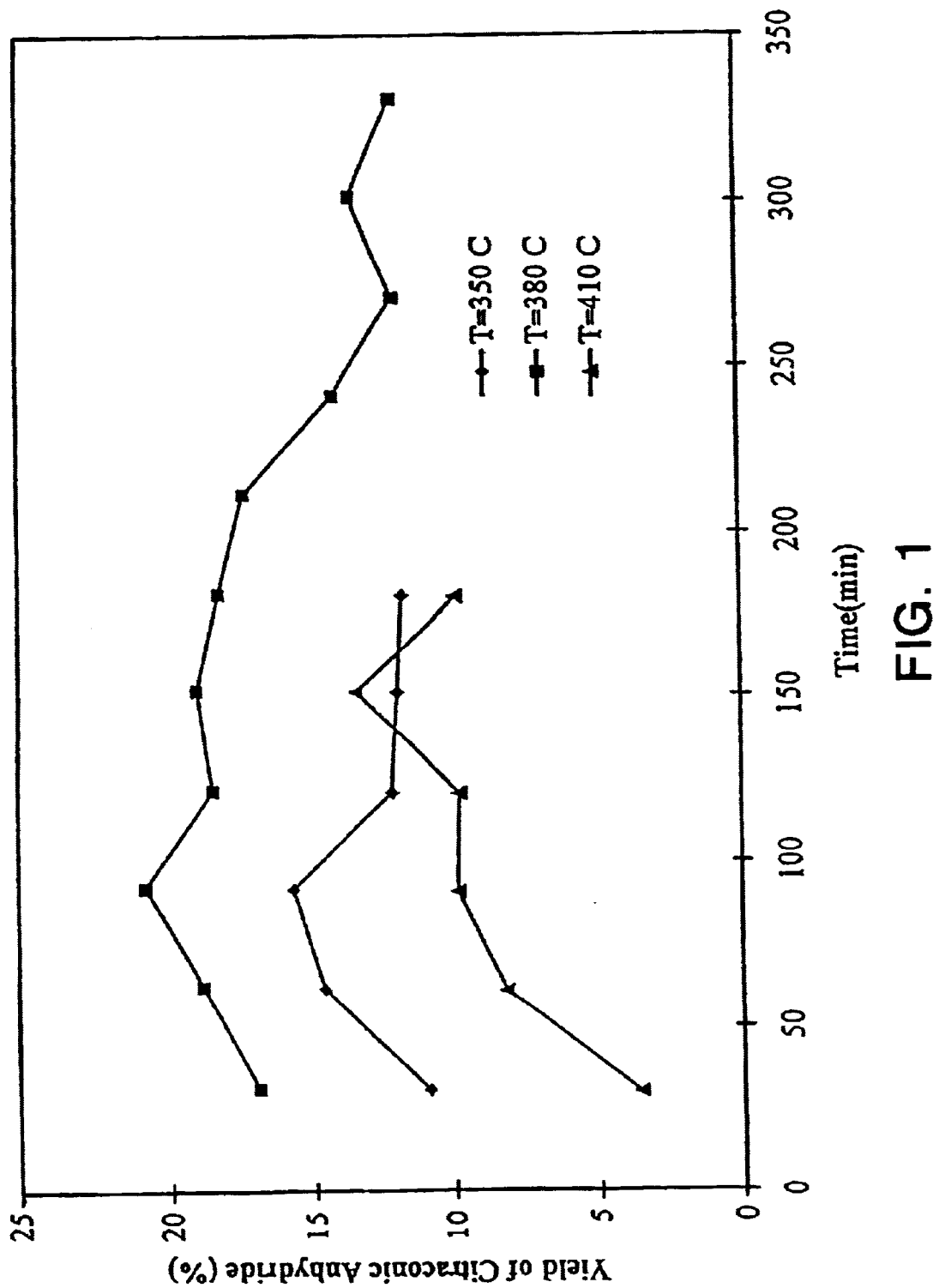
FIG. 1 is a graph showing the yield of citraconic anhydride at various temperatures using a porous gamma alumina catalyst (SA3177).

Several different forms of succinate were used as feedstocks in these investigations. Dimethyl succinate (DMS) was used in most reactions. Diethyl succinate (DES) was used briefly but led to complications in analysis because it transesterified to methyl ethyl succinate in the presence of methanol formed from formaldehyde during reaction. Succinic anhydride was used in a series of reactions, both in its neat form and dissolved into methanol to form monomethyl succinate.

Formaldehyde was used in one of three forms Initially, 1,3,5 trioxane, the trimeric form of formaldehyde, was used because of its ease in handling. In more recent studies, formalin, a commercially available source containing 37 wt % formaldehyde and 10% methanol in water was used. Another solution consisting of 55% formaldehyde, 35% methanol, and 10% water was used. Other sources of formaldehyde, such as pure, gaseous formaldehyde obtained from decomposition of paraformaldehyde, could also be used for the reaction.

Catalysts and Catalyst Preparation

A number of catalyst materials have proven effective for the condensation of succinates and formaldehyde to citraconic and itaconic acids. These catalysts consist of metal oxide ceramics with weak Lewis acid and base surface sites that appear critical for efficiently catalyzing the condensation between succinates and formaldehyde. In prior art, such materials have been used as support materials for catalysts consisting of metal salts impregnated onto the ceramic. Such salt-impregnated catalysts were made in this study and no advantage was found in adding the salt. In contrast, the best yields were obtained when the support metal oxide alone is used. The ceramic metal oxide catalysts used were obtained from commercial venders or have been prepared.

Several types of commercial aluminum oxide (Al$_2$O$_3$) were obtained from Norton Chemical Process Product Corporation (Akron, Ohio) for use as catalysts. These include the Norton materials specified as SA 3132, SA 3177, SA 6175 and SA 6173. These alumina materials were ground to −30+60 mesh and calcined for 12 hours at 500° C. overnight before loading into the reactor. Zirconia supports manufactured by MEI, Inc. (Flemington, N.J.) were also evaluated;

this zirconia had about 15 wt % alumina as a binder. Magnesium oxide and iron oxide (Aldrich Chemical Co., Milwaukee, Wis.) were also tested. Properties of these catalyst materials are given in Table 1 hereafter.

A number of metal oxides were prepared and evaluated as catalysts for the condensation reaction. These include alumina, titania, aluminum phosphates, and hydrotalcites (MgO/Al$_2$O$_3$ compounds). Properties of these materials are also given in Table 1.

Typical preparation procedures for these materials are given in the following paragraphs:

Aluminum oxide: Aluminum oxide was prepared by dissolving 60 g of aluminum chloride in 800 ml of water. The pH of initial solution was about 2.2. The solution was filtered to remove any suspended impurities and then precipitated with 100 ml of 25% ammonia solution to a pH of 9. The precipitate was aged overnight, filtered, and washed free of chloride ions. The residue was dried overnight in an oven at 110° C. and then calcined at 400° C. for 3 hours. The weight of calcined catalyst was 16.75 g.

Titanium oxide: Titania was prepared from titanium (IV) butoxide by dissolving it in water and acidifying it with HNO$_3$ until a clear solution was obtained. Thus, 63 g of titanium butoxide was dissolved in 500 ml water and acidified with 60 ml HNO$_3$. The initial pH of the solution was 0.66. This solution was precipitated with ammonia until pH 7.0. The residue was washed with water and dried at 110° C. overnight and calcined at 400° C. for 3 hours. The final weight of catalyst after calcination was 15.95 g.

Preparation of alumina-magnesia coca talyts: Al—Mg oxide cocatalysts were prepared from gels produced by mixing two solutions according to the procedure described by Corma et al. (Corma, A., Fornes, V., Rey, F. J. Catal. 148 205–212 (1994)). Solution A was prepared by mixing MgCl$_2$ and AlCl$_3$ to a concentration of 1.5 M in Al+Mg with Mg/(Al+Mg) atomic ratios either 0.25, 0.5, or 0.75. Solution B was prepared by dissolving Na$_2$CO$_3$ to a concentration of 1M and adding NaOH to get a pH of 13. Solution B was added to solution A under vigorous stirring for a period of 2 to 3 hours. The gels were aged overnight, filtered, washed free from Cl$^-$, and calcined at 450° C. in air for 6 hours to get Mg—Al mixed oxides of the stated ratios.

For example, a catalyst preparation with Mg/(Al+Mg)= 0.25 involved dissolution of 1.78 g of MgCl$_2$ and 14.30 g of AlCl$_3$ in 60 ml water. In solution B, 5.6 g of Na$_2$CO$_3$ and 3.5 g of NaOH was dissolved in 50 ml water to make a solution that was 0.1 M in Na$_2$CO$_3$ at pH 13. The latter solution was mixed into the former over a period of 2 hours, wherein a gel was obtained and the final pH was 10. The gel was aged overnight and washed with deionized water until the residual filtrate was free of Cl$^-$ ions. The residue was dried overnight and calcined at 450° C. for 6 hours. The weight of the final catalyst was 3.6 g. A similar procedure was followed for preparing catalysts with Mg/(Al+Mg) atomic ratios 0.5 and 0.75.

A different method was followed for the preparation of magnesia-alumina co-catalysts with low quantities of magnesia. Mg—Al mixed oxides with Mg/(Mg+Al) ratios of 0.005, 0.01, 0.02, 0.04, 0.06, 0.1 and 0.12 were prepared using aqueous solutions of aluminum nitrate and magnesium chloride and coprecipitated with NH$_3$. The residue was filtered and washed free from chloride and later calcined in air at 350° C. As an example, a magnesia-alumina co-catalyst with a Mg/(Mg+Al) ratio of 0.02 was prepared by dissolving 110.3 g of aluminum nitrate and 0.63 gm of magnesium chloride in 800 ml water. The initial pH of the solution was 1.8. The solution was precipitated with 25% ammonia over a period of 2 hours until a pH of 9.0 was attained. This required about 85 ml of ammonia. The gel was aged overnight, washed free from chloride, dried at 100° C. overnight, and calcined at 350° C. for 3 hours. The weight of the final catalyst after calcination was 15.50 g. A similar procedure was followed while preparing catalysts with Mg/ (Mg+Al) ratios of 0.005, 0.01, 0.04, 0.06, 0.1 and 0.12. The molarity of the precipitating solution was maintained constant when catalysts with varying Mg content were prepared.

Aluminum phosphates: Aluminum phosphates (ALPO) were prepared by the method followed by Rebenstorf et al (Rebenstorf, B., Lindbald, T., Anderson, K. J. Catal. 128 293–302 (1991)). The precursors for the preparation of ALPO were Al(NO$_3$)$_3$ and (NH$_4$)$_2$HPO$_4$. P/Al ratios of 0.5, 0.8, 1.0 and 1.5 were prepared by dissolving the precursors in water and acidifying the solution with HNO$_3$ until the solution was clear and then precipitating it with ammonia until a pH of 5 was attained. The resultant residue was filtered, washed with water, dried at 120° C. overnight, and calcined at 400° C. for 3 hours. As an example, an ALPO with P/Al ratio of 0.5 was prepared by dissolving 75 g of aluminum nitrate nonahydrate and 11.5 g of ammonium hydrogen phosphate in 800 ml of water. Acidifying the solution with nitric acid dissolved any insoluble white residue that was formed during the process. About 22 ml nitric acid was required for dissolving the precipitate. The pH of this solution was 0.5. This solution was precipitated with 49 ml ammonia (25%) until pH 5. The final residue was washed with 4 liters of water, dried in an oven at 110° C. overnight, and calcined at 400° C. for 3 hours.

Supported salt catalysts: Several supported catalysts were prepared by the incipient wetness method. A salt solution of predetermined concentration, in an amount just sufficient to fill the pores and wet the outside of the particle, was introduced into the support. The wetted support oxide was then dried slowly to properly crystallize the salt on the support surface. The dry mixture was then calcined in a furnace at 450° C. for 4 to 5 hours. The supported salts include Ce (SO$_4$)$_3$, ZnCl$_2$ KH$_2$PO$_4$, LaCl$_3$, Li$_2$CO$_3$, K$_2$CO$_3$ and KOH. The quantities of these salts on the support oxides varied; specific loadings are given in the Results.

Apparatus

Figure 8:
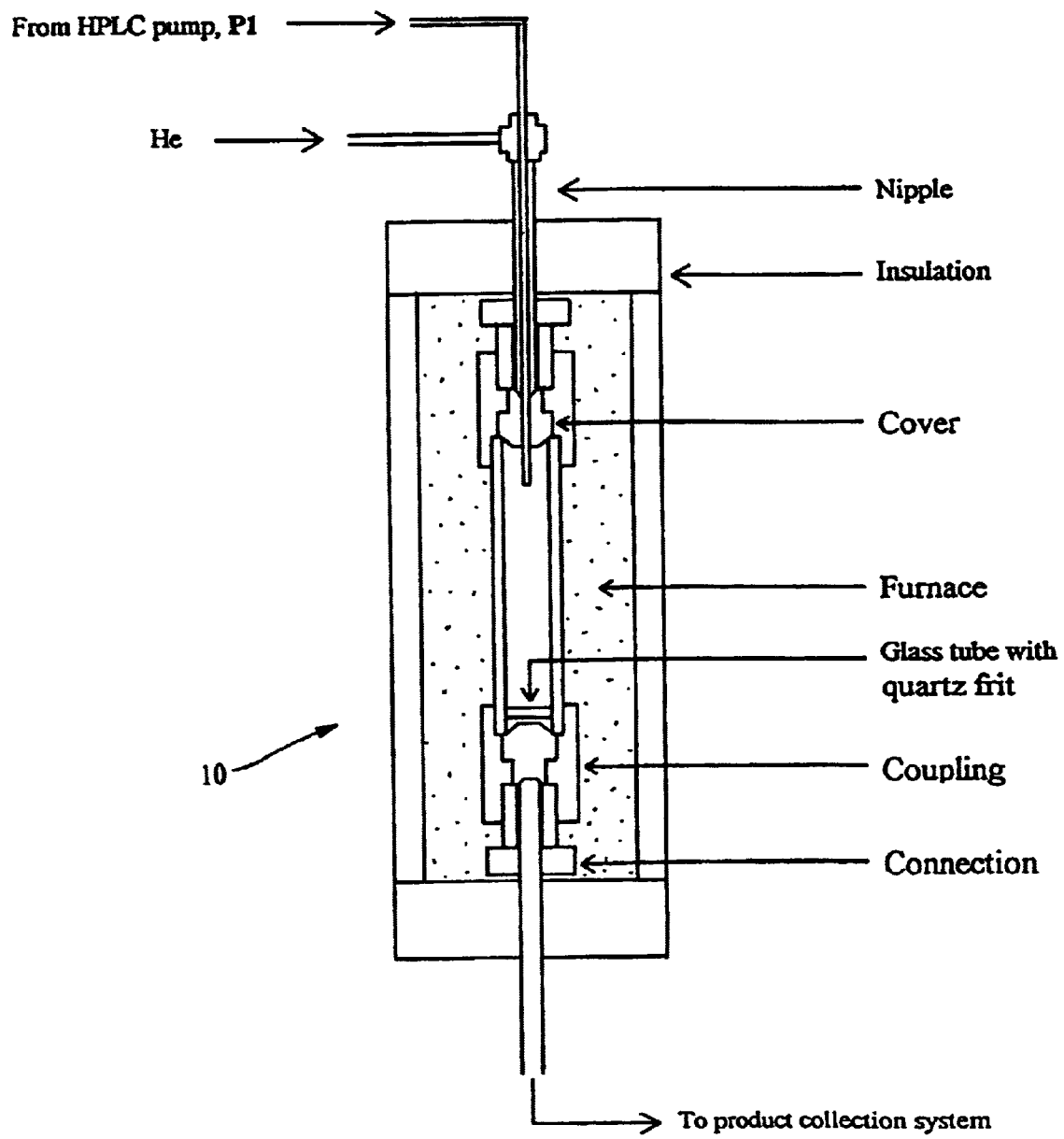
FIG. 8 is a schematic view of the commercially available vapor phase reactor 10.

A fixed bed reactor system (FIG. 9) has been designed and constructed to operate continuously at a temperature range of 300–500° C. and at pressures up to 500 psi. An Autoclave Engineers (Erie, Pa.) cone closure tubing reactor vessel 10 (Part# CC.985SS20), made of 316 stainless steel, was used as the reactor vessel 10 (FIG. 8). The length, outer diameter, and internal diameter of the reactor vessel 10 are 102 mm, 19.1 mm, and 11.1 mm, respectively. The nominal capacity of the reactor is 9.85 milliliters. The catalyst was held in the reactor by a quartz frit fitted into a 5 mm long by 10-mm OD quartz tube. The reactor vessel 10 was heated by clamshell heaters controlled by an Omega series CN-2010 programmable temperature controller. The surface temperature of the reactor 10 was used as the control thermocouple.

Figure 9:
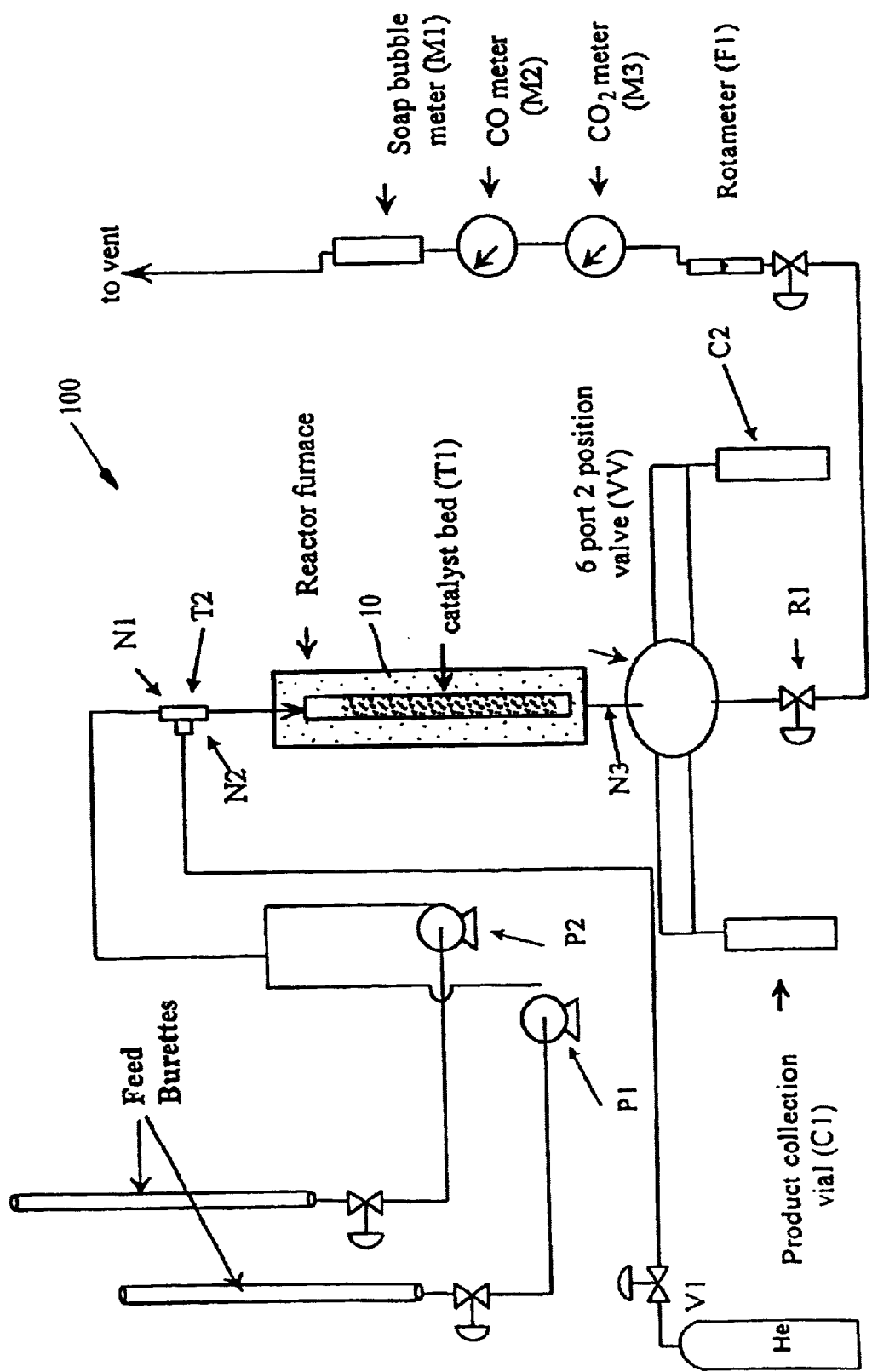
FIG. 9 is a schematic view of the reactor 10 converted for the vapor phase reaction.

Feeds for the reaction were held in burettes and were introduced into the reactor vessel 10 using one or two Bio-Rad (Hercules, Calif.) Soft-Start HPLC Pumps P1 and P2 (FIG. 9). The choice of liquid feeds dictates the feed arrangement used. If Formalin is used with succinic acid esters as feedstocks, then each reactant is pumped by a separate Bio-Rad pump P1 or P2. If trioxane, which is soluble in diethyl succinate and dimethyl succinate, was used as a formaldehyde source, then the feeds were combined and only a single pump is used. In this case, the feed line was heated to 70° C. using heating tapes and a variable autotransformer to prevent solidification of trioxane. In all cases, the 60 cm of feed tubing just before the reactor vessel 10 inlet was heated at 250° C. using heating tape. Helium was used as a carrier gas in most experiments to aid in vaporization of feeds and to sweep the vaporized feed into the reactor.

Reactor effluent exits the reactor via a heat-traced tube N3 and enters a 6-port valve VV (Valco, Inc., Houston, Tex.); this valve directs products to one of two product collection traps C1 or C2 consisting of 25 ml Stainless Steel sample cylinders immersed in water. The reactor outlet tube N3 and 6-port valve VV are maintained at 200° C. using 0.5 inch heating tape to keep product in the vapor phase above the traps C1 and C2. Riken (Japan) Infrared Gas Analyzers M2 and M3 are used to analyze carbon dioxide and carbon monoxide concentrations in the exiting gas. The exiting gas flow rate is controlled by a metering valve R1 and measured using a soap bubble meter M1.

Operating Procedure and Conditions

A desired quantity of precalcined catalyst material (usually 5.0 g) was added through the top of the reactor vessel 10. After the reactor vessel 10 was sealed, helium was fed into the reactor to the desired pressure using the cylinder regulator V1. The reactor vessel 10 tubing was then heated to the desired temperature and allowed to stabilize for one hour. Liquid feed(s) were then pumped into the reactor at the desired flow rate. Liquid flow rate was set with the digital meter in the pump, but actual flow rate was calculated by measuring the differential volume of liquid fed from the burette over time. The product was collected in the product traps C1 and C2 for 15–30 minute intervals once steady state conditions were achieved; products were removed at the end of the collection period for analysis. Upon completion of a run at a specified set of conditions, either new conditions (temperature, pressure, flow rate) were established or the liquid feeds were shut off and the reactor vessel 10 was cooled under helium. The catalyst was removed and weighed at the end of the run.

The reaction conditions that were used included temperatures from 320 to 450° C. with a preferred range of 350–380° C., pressure from 40 to 400 psi, with a preferred value of 60 psig, liquid flow rate of 0.1 to 0.5 ml/min and a succinate:formaldehyde ratio of 1:0.5 to 1:4. The "base case" conditions for the experiments conducted are 60 psig (0.5 Mpa absolute), a total liquid flow rate of 0.12 ml/min, a gas flow rate of 25 ml (STP)/min, a catalyst quantity of 5.0 g, a succinate:formaldehyde ratio of 1:2, and a temperature of 380° C. At these conditions, the weight hourly space velocity (WHSV) is 0.6 kg succinate/kg catalyst/hr.

Product Analysis

High-pressure liquid chromatography (HPLC) and gas chromatography (GC) were used to identify and separate the reaction products. For HPLC, a Bio-Rad HPX-87H organic acid column was used with an UV detector and a RI detector in a series for the product identification using oxalic acid as an internal standard. A solution of 20% acetonitrile and 5 mM sulfuric acid in water served as the mobile phase. GC analysis was performed using a sample injected into an intermediate capillary column of diameter 0.53 mm and length of 30 m (SPB-1, Supelco, Bellefonte, Pa.). The column was installed in a Varian 3300 GC (Sunnyvale, Calif.) with flame ionization detector and helium as a carrier gas. Methyl lactate was used as an internal standard. Product identification was conducted by matching residence times in GC and HPLC, and by combined gas chromatography-mass spectroscopy (GC/MS) in a separate instrument. Product yields were obtained by using peak areas of product species and response factors obtained from standard solutions. Results were placed in a spreadsheet to facilitate ready calculation of yield, selectivity, and conversion, and an overall carbon balance on the system was performed.

Results

Catalytic Conversion of Succinate to Citraconate

The properties of the catalysts obtained from commercial sources or prepared by the methods described above have been characterized for their surface area and acid/base properties. Total surface area measurements were conducted by nitrogen adsorption according to the standard BET method. Acid site concentration and strength on the catalyst surface was measured by temperature programmed desorption (TPD) of ammonia using a Micromeritics Chemisorb 2700. Base site concentration was determined by TPD of carbon dioxide in the same instrument. Acid site strength and base site strength were further characterized by adsorption of Hammett indicators in dry benzene. Results of these characterization measurements are given in Table 1 hereinafter for the catalysts used.

Results of citraconic anhydride formation from succinate and formaldehyde presented here represent the most promising catalysts and conditions for the reaction. Over 150 experiments have been performed, with many experiments giving only a few percent conversion to citraconic anhydride. In the results, yield of citraconic anhydride or acid is defined as a percent of theoretical, or [moles of total citraconate formed/mole succinate fed to the reactor] multiplied by 100. Conversion is the fractional conversion of succinate in the reactor, [(moles succinate fed-moles succinate out)/moles succinate fed]. Selectivity is defined as [moles of total citraconate formed/mole succinate converted]. The conversion of dimethyl succinate to monomethyl succinate and succinic acid is not considered part of "succinate conversion", because these species are recycled along with unreacted dimethyl succinate in the process. Finally, a balance on total succinate carbon is done for the experiment as a measure of the quality of the experiment. Results are reported as the percentage of initial succinate carbon recovered in the product mixture.

Most generally, the raw product exiting the reactor is a mixture of citraconic anhydride, citraconic acid, monomethyl citraconate, and dimethyl citraconate. Analysis of all of these compounds is difficult as several of the products co-elute with monomethyl or dimethyl succinate. To clearly evaluate product yields and selectivity, it is necessary to hydrolyze the product mix in aqueous $H_2SO_4$ solution to recover all species as the free acid. Unless otherwise noted, all yields and selectivities are based on the hydrolyzed products. Usually, about 20% of the citraconate is in the form of monomethyl or dimethyl ester, so reported yields for unhydrolyzed mixtures are lower than the actual values.

The rate of formation of citraconic anhydride in the reactor declines after several hours on line as the catalyst cokes and thus deactivates. It appears that coking involves both the succinate species and formaldehyde. The rate of coking is high early in the reaction according to weight gain of the catalyst taken at different times during reaction. The production of CO and $CO_2$ is also very high early in the reaction, and then declines to a small value after about 30 min. The extent of coking is less when Formalin is used as the formaldehyde source, because water passing through the reactor steam cleans the catalyst. In some of the results, yield is reported as a function of reaction time to illustrate this deactivation. In other experiments, only the maximum yields achieved are reported.

Figure 2:
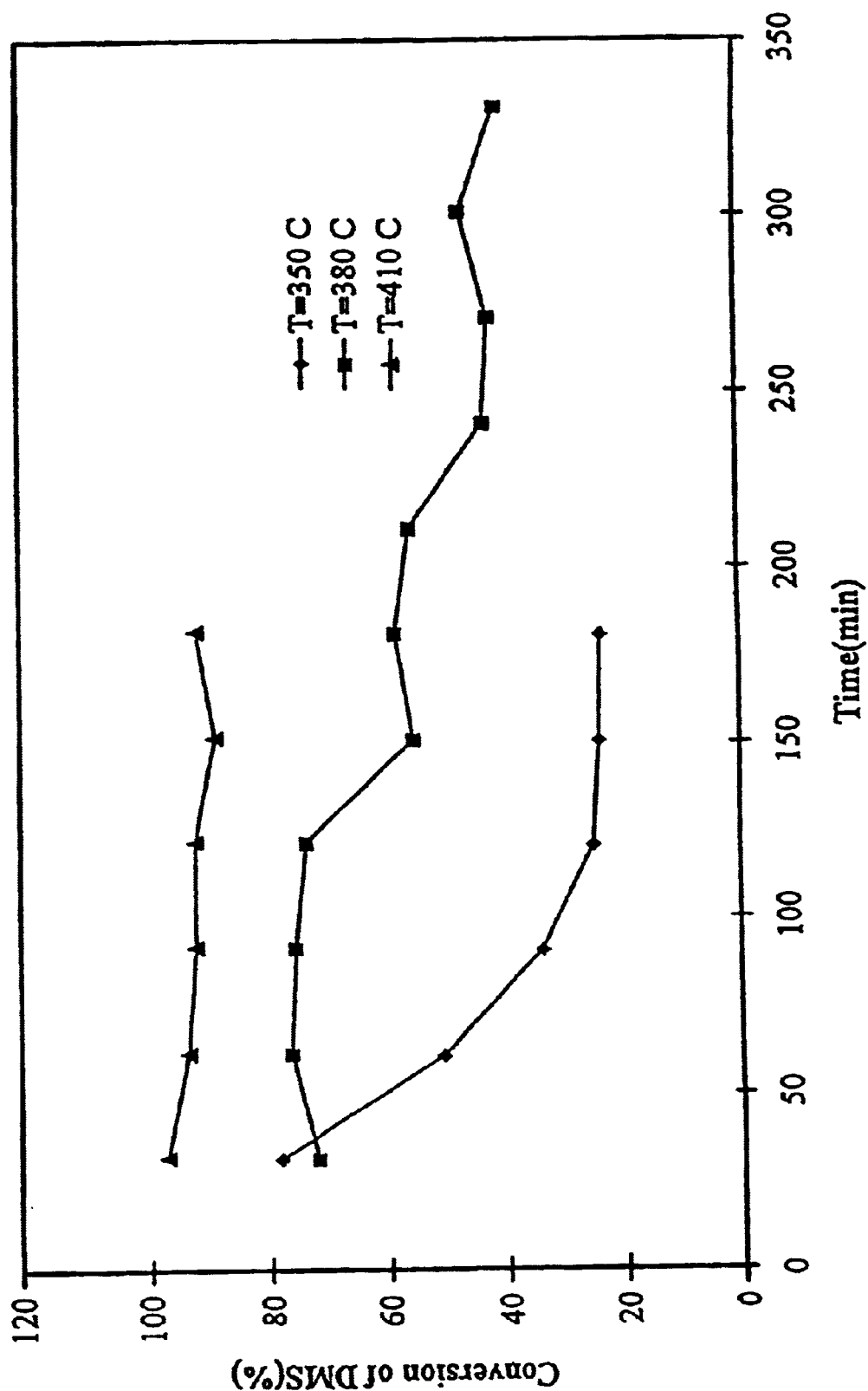
FIG. 2 is a graph showing the conversion of dimethylsuccinate to citraconic anhydride using the porous gamma alumina catalyst (SA3177) of FIG. 1.

The effect of temperature on citraconic anhydride yield (unhydrolyzed results) and dimethyl succinate conversion is given in FIGS. 1 and 2. The values (unhydrolyzed results) are also given in Table 2. In this experiment, all conditions are at the base-case values except temperature. Trioxane dissolved into DMS was used as the formaldehyde source. The catalyst used was Norton alumina SA3177. Citraconic anhydride yields are clearly highest at 380° C.; at temperatures above 380° C. secondary reactions and competing reactions, especially the Canizzaro reaction of formaldehyde, predominate over the desired condensation. At lower temperatures the conversion is lower (FIG. 2). It is worth noting that selectivity to citraconic anhydride is highest at 350° C. The only side products produced are CO and $CO_2$; other than that dimethyl succinate is only converted to monomethyl succinate and succinic acid, both of which can be recovered in the process.

Figure 3:
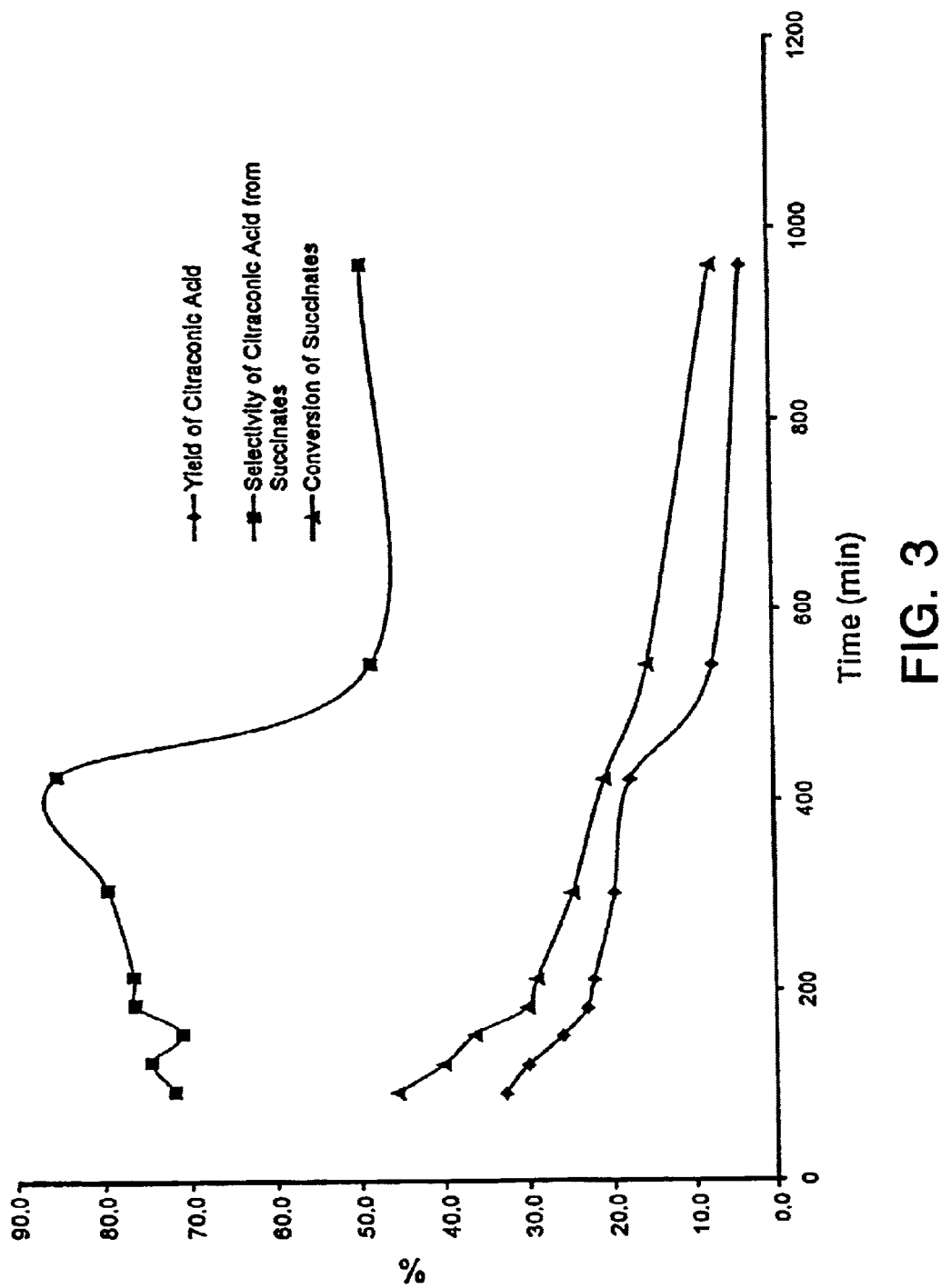
FIG. 3 is a graph showing the results of an extended continuous run (17 hours) using the porous gamma alumina (SA3177) of FIG. 1.

The full time scale of catalyst deactivation is shown in an extended time experiment in FIG. 3 and in more detail in Table 3, again at base-case conditions. Trioxane and DMS are feed materials, and Norton SA3177 alumina is used as catalyst. It is clear that conversion of succinate and yield of citraconate (hydrolyzed results) decay over the 16 hour run. Selectivity in this run, however, is consistently high at between 70 and 80%. The carbon recovery ranges from 80% to 95%, indicating that the experiments are of good quality. It is noteworthy that the deficit in carbon recovery results in lower yields and selectivities; if all carbon were accounted for the values of yield and selectivity reported can only increase.

Upon deactivation, the alumina catalyst can be regenerated by exposure to air at 500° C. for several hours or until no $CO_2$ is evolved. The yields of citraconic anhydride are virtually identical before and after the regeneration process, as seen in Table 4. These experiments demonstrate the robust nature of the oxide catalysts and their ability to be regenerated.

The use of succinic anhydride as a feed for the reaction has been investigated in detail. Results of a typical experiment are given in Table 5; reaction conditions are at base case values with trioxane as the formaldehyde source and Norton SA3177 as the catalyst. The feed, a molten mixture of succinic anhydride and trioxane, was maintained at 120° C. in a syringe pump before being fed to the reactor. The yield of citraconate following hydrolysis is as high as 43% of theoretical, with selectivity ranging from 50–70% except at the very beginning and end of the experiment. The yield of $CO_2$ is significantly higher using succinic anhydride than with dimethyl succinate, resulting in lower selectivities. The only other succinate formed is monomethyl succinate (MMS), resulting from the reaction of succinic anhydride with methanol formed from formaldehyde via the Canizzaro reaction.

In a second set of experiments, succinic anhydride was mixed with methanol and trioxane to make a feed mix of monomethyl succinate and trioxane. Reaction temperature was 350° C. for this reaction, the flow rate was 0.3 ml/min and the catalyst was again Norton SA3177. Results are given in Table 6; succinate conversion is lower with this feed mixture and conditions but selectivity is better at 75–80%. Thus, succinic anhydride is a good feed material for the reaction, as the highest yields of citraconate were achieved with very good selectivities. In the laboratory, reactions are somewhat more difficult to conduct with succinic anhydride, because it has a very high boiling point (269° C.) and solidifies on encountering a cold spot or surface. This led to frequent plugging of reactor tubes and collection traps during experiment. On a commercial scale, the properties of succinic anhydride should pose less of a problem.

The use of Formalin, a mix of 37 wt % formaldehyde, 10 wt % methanol, and 53 wt % water as a formaldehyde source is demonstrated in Table 7. This reaction was conducted at base case conditions using Norton SA3177 alumina as a catalyst. Selectivity of 60% is achieved with a citraconate yield of 26–28%. Two advantages of using Formalin are apparent: first, the decay in catalyst activity is much slower with Formalin; yield only drops off very slowly over time for reaction times out to 5 hours. Second, the gain in catalyst weight due to coking is much less with Formalin, likely because the water present steam cleans the catalyst during reaction.

The use of Formcel, a mix of 55 wt % formaldehyde, 35 wt % methanol, and 10 wt % water is demonstrated in Table 8. Results similar to those obtained with Formalin are obtained, with low $CO_2$ yield and selectivity as high as 70%. More monomethyl succinate was formed than with Formalin, however, a consequence of the higher methanol content in the feed.

The above reactions were all conducted using Norton SA3177 alumina as the catalyst in the reactor. This material was found early on to be the best material for the reaction, and most of the studies were completed with it as the catalyst. Other materials have been tested: Table 9 gives the yield of citraconic anhydride (unhydrolyzed results) over several other aluminas and ceramic oxide materials. All of these runs were conducted at the "best case" conditions. It is seen that the other Norton aluminas, alumina prepared, and aluminum phosphate (ALPO) are quite effective catalysts, nearly the same as Norton SA3177. The zirconia and zeolites are less effective. Experiments with iron oxides and magnesium oxide gave essentially no citraconic anhydride.

Figure 4:
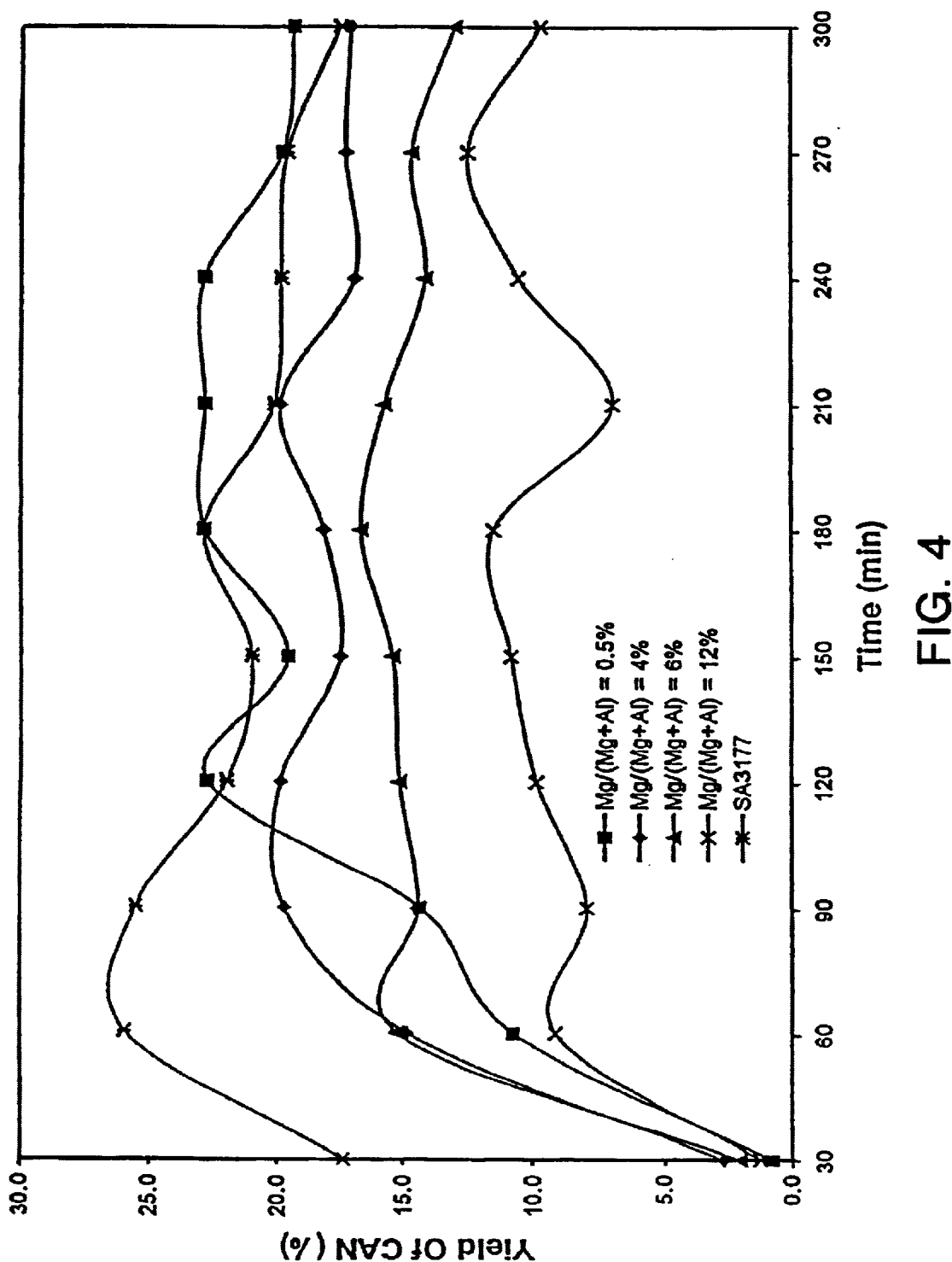
FIG. 4 is a graph showing the yield of citraconic anhydride (CAN) from different magnesium-aluminum oxides as a function of time.
Figure 5:
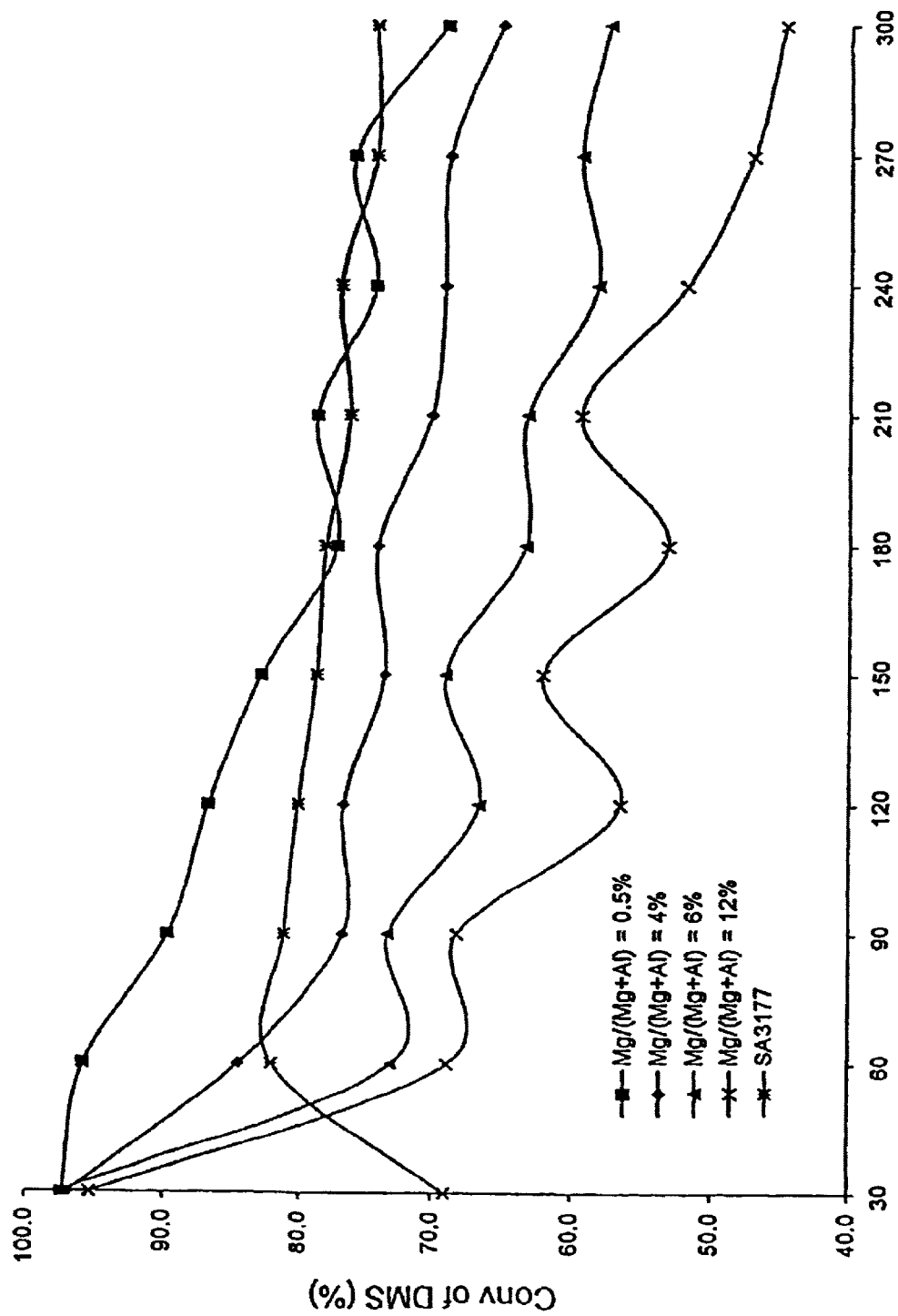
FIG. 5 is a graph showing the percentage conversion of dimethylsuccinate (DMS) with different magnesium-aluminum oxides.

Compounds of MgO and $Al_2O_3$, are interesting catalysts for study because they can be prepared in different Mg:Al ratios to give different surface acidities. Results for a set of these magnesia-alumina cocatalysts prepared are given in FIGS. 4 and 5. The measured acidity and basicity of the cocatalysts prepared are given in Table 1. As the Mg content of the material increases, the conversion of DMS and the yield and selectivity for citraconate formation decline. Yields for a Mg—Al cocatalyst containing 25% Mg gave essentially no citraconate; cocatalysts containing 0.5%, 1%, and 3% Mg gave the same results as the prepared alumina.

The results observed with magnesia-alumina cocatalysts are in accord with those of other catalysts regarding the surface acidity/basicity properties required for an active catalyst. First, active catalysts must have a significant concentration of mildly or weakly acidic surface sites. Strong acid sites only, such as those found on the Zeolite 13X, lead primarily to cracking of DMS to $CO_2$. The second requirement is that the catalyst does not have a high concentration of strong basic sites. These strong basic sites catalyze the Cannizaro reaction of formaldehyde to form ultimately $CO_2$ and methanol, thus preventing formaldehyde from participating in the desired condensation.

Table 10 summarizes all of the runs to date with the catalyst of the present invention and other catalysts which were not effective.

TABLE 1

Properties of catalysts used for catalytic condensation

| S.N. | Catalyst | S. A. (m²/g) | Acid Strength (pk$_a$) | Acid site density (mmol/g) | Basic site density (mmol/g) |
|---|---|---|---|---|---|
| 1 | AlPO, P/Al ratio | | | | |
| A | 0.5 | 150 | −0.2 to −3.2 | 0.582 | — |
| B | 0.8 | 137 | −0.2 to −3.2 | 1.220 | — |
| C | 1.0 | 156 | −0.2 to −3.2 | 2.345 | — |
| D | 1.5 | 76 | −0.2 to −3.2 | 1.810 | — |
| 2 | Alumina, MSU | 173 | +1.1 to −0.2 | 0.671 | 0.150 |
| 3 | Alumina, Norton | | | | |
| A | SA3132 | 32 | — | — | — |
| B | SA3177 | 107 | +1.1 to −0.2 | 0.250 | 0.050 |
| C | SA6173 | 220 | — | — | — |
| D | SA6175 | 236 | −0.2 to −3.2 | — | 0.091 |
| 4 | Hydrotalcites, % Mg | | | | |
| A | 0.5 | 163 | +2.4 to −1.2 | 0.608 | 0.157 |
| B | 1 | 178 | +2.4 to −1.2 | 0.646 | 0.161 |
| C | 2 | 150 | +2.4 to −1.2 | 0.782 | 0.220 |
| D | 4 | 174 | +2.4 to −1.2 | 1.020 | 0.195 |
| E | 6 | 176 | +2.4 to −1.2 | 0.676 | 0.141 |
| F | 10 | — | — | — | — |
| G | 12 | 171 | +2.4 to −1.1 | 0.704 | 0.260 |
| H | 25 | | — | — | — |
| I | 75 | 143 | +2.4 to −1.1 | — | — |
| 5 | Iron oxide | — | — | — | — |
| 6 | Magnesia | 0.77 | >+4.8 | 0 | 0.196 |
| 7 | Titania | 45 | +2.4 | 0.122 | 0.007 |
| 8 | Zirconia, MEI Inc | 62 | +2.4 | 0.066 | 0.068 |
| 9 | Zirconia, MSU | — | — | — | — |

Notes:
1 Surface areas determined by nitrogen BET.
2 Acid strengths determined by titration with Hammett indicators.
3 Acid and basic site densities determined by ammonia and carbon dioxide temperature programmed desorption (TPD).

TABLE 2

Yield of citraconic anhydride and conversion of DMS at various temperatures (Results before hydrolysis)[a]

| Elapsed Time (min) | Yield of citraconic anhydride (%) @ 350° C. | @ 380° C. | @ 410° C. | Conversion of DMS (%) @350° C. | @380° C. | @410° C. |
|---|---|---|---|---|---|---|
| 30 | 11.0 | 16.9 | 3.6 | 78.2 | 72.0 | 97.1 |
| 60 | 14.6 | 18.9 | 8.1 | 50.6 | 76.4 | 93.7 |
| 90 | 15.7 | 20.8 | 9.8 | 33.6 | 75.6 | 92.4 |
| 120 | 12.2 | 18.5 | 9.7 | 25.1 | 73.8 | 92.4 |
| 150 | 12.0 | 19.0 | 13.4 | 24.0 | 55.3 | 89.1 |
| 180 | 11.8 | 18.3 | 9.8 | 23.8 | 58.3 | 92.1 |
| 210 | | 17.4 | | | 55.8 | |
| 240 | | 14.2 | | | 43.2 | |
| 270 | | 12.1 | | | 42.2 | |
| 300 | | 13.5 | | | 46.8 | |
| 330 | | 12.1 | | | 40.8 | |

[a]Reaction Pressure = 60 psi; feed = DMS + 1,3,5-trioxane (TO); liquid feed flow rate = 0.10 ml/min; molar ratio = 2/3 to 1 (TO to DMS)

TABLE 3

Results from Extended Run (17 hrs)[a]

| Elapsed Time (min) | Yield of Citraconates (%) | Conversion of Succinates (%) | Selectivity[b] (%) | Yield of CO$_2$ (%) | Carbon Recovered[c] (%) |
|---|---|---|---|---|---|
| 90 | 32.8 | 45.6 | 71.9 | 21.1 | 85.5 |
| 120 | 30.0 | 40.2 | 74.6 | 22.6 | 89.1 |
| 150 | 26.0 | 36.6 | 71.0 | 15.4 | 84.6 |
| 180 | 23.0 | 30.1 | 76.4 | 9.9 | 81.0 |
| 210 | 22.2 | 29.0 | 76.6 | 10.2 | 78.0 |
| 300 | 19.6 | 24.7 | 79.4 | 8.1 | 78.0 |
| 420 | 17.6 | 20.7 | 85.0 | 7.5 | 95.0 |
| 540 | 7.5 | 15.5 | 48.4 | 8.5 | 82.0 |
| 750 | 6.0 | 6.5 | 92.3 | 4.8 | 92.3 |
| 960 | 3.6 | 7.3 | 49.3 | 4:5 | 87.0 |

[a]Reaction temperature = 380° C.; pressure = 60 psi; feed = DMS + 1,3,5-trioxane (TO) liquid feed flow rate = 0.10 ml/min; molar ratio = 2/3 to 1 (TO to DMS)
[b]Selectivity of Citraconates = Yield of Citraconates * 100/(Conv of DMS − Yield of SA − Yield of MMS)
[c]Carbon recovered (%) = 100 − (moles of C in − moles of C out) * 100/ moles of C in

TABLE 4

Yield of citraconic anhydride[a] before and after the regeneration[b] of catalyst

| Elapsed Time (min) | Yield of Citraconic Anhydride (%) Before | After | Yield of CO$_2$ (%) Before | After | Conversion of DMS (%) Before | After |
|---|---|---|---|---|---|---|
| 30 | 14 | 10 | 11 | 12 | 77 | 74 |
| 60 | 13 | 13 | 5 | 5 | 57 | 62 |
| 90 | 11 | 11 | 8 | 8 | 60 | 63 |
| 120 | 11 | 11 | 4 | 3 | 54 | 60 |
| 150 | 11 | 11 | 6 | 6 | 58 | 60 |
| 180 | 11 | 12 | 4 | 3 | 56 | 53 |
| 210 | 11 | 11 | 5 | 3 | 50 | 54 |

[a]Reaction temperature = 380° C.; pressure = 60 psi; feed = DMS + Formalin; liquid feed flow rate = 0.20 ml/min; molar ratio = 0.5 to 1 (formaldehyde to DMS)
[b]The catalyst was regenerated by flowing air through the reactor for 6 hrs at 500° C..

TABLE 5

Citraconic Acid from Succinic Anhydride[a]

| Elapsed Time (min) | Yield of Citraconic Acid (%) | Yield of MMS (%) | Yield of $CO_2$ (%) | Conversion of Succinic Anhydride (%) | Selectivity[b] (%) | Carbon Recovered[c] (%) |
|---|---|---|---|---|---|---|
| 30 | 25 | 3 | 42 | 84 | 31 | 70 |
| 60 | 43 | 6 | 33 | 80 | 58 | 87 |
| 90 | 43 | 6 | 24 | 75 | 62 | 81 |
| 120 | 29 | 7 | 24 | 41 | 71 | 93 |
| 150 | 18 | 6 | 20 | 63 | 32 | 67 |

[a]Reaction temperature = 380° C.; pressure = 60 psi; feed = Succinic Anhydride + 1,3,5-trioxane (TO); liquid feed flow rate = 0.10 ml/min; molar ratio = 2/3 to 1 (TO to Succinic Anhydride)
[b]Selectivity of Citraconic Acid = Yield of Citraconic Acid * 100/(Conv of SAn − Yield of MMS)
[c]Carbon recovered (%) = 100 − (moles of C in − moles of C out) * 100/moles of C in

TABLE 6

Citraconates from MMS[a] (Results after hydrolysis)

| Elapsed Time (min) | Yield of citraconates (%) | Yield of CO2 (%) | Conversion of succinates (%) | Selectivity[b] (%) |
|---|---|---|---|---|
| 30 | 25 | 15 | 50 | 50.0 |
| 60 | 31 | 15 | 40 | 77.5 |
| 90 | 25 | 5 | 33 | 75.8 |

[a]Reaction temperature = 350° C.; pressure = 60 psi; feed = 34 wt % MMS (succinic anhydride was dissolved in excess of methanol) + 51 wt % methanol + 15 wt % 1,3,5-trioxane (TO); liquid feed flow rate = 0.30 ml/min; molar ratio = 2/3 to 1 (TO to MMS)
[b]Selectivity of Citraconates = Yield of Citraconates * 100/(Conv of MMS − Yield of DMS − Yield of SA)

TABLE 7

Citraconates from DMS and Formalin[a] (Results after hydrolysis)

| Elapsed Time (min) | Yield of Citraconates (%) | Yield of CO2 (%) | Conversion of Succinates (%) | Selectivity[b] (%) |
|---|---|---|---|---|
| 60 | 26 | 7 | 43 | 61 |
| 90 | 28 | 10 | 50 | 56 |
| 180 | 26 | 4 | 46 | 57 |
| 240 | 25 | 6 | 42 | 60 |

[a]Reaction temperature = 380° C.; pressure = 60 psi; feed = 47 wt % DMS + 6 wt % methanol + 20 wt % formaldehyde + 27 wt % water; liquid feed flow rate = 0.15 ml/min; molar ratio = 2 to 1 (formaldehyde to DMS)
[b]Selectivity of Citraconates = Yield of Citraconates * 100/(Conv of DMS − Yield of SA − Yield of MMS)

TABLE 8

Citraconates from DMS and Formcel[a] (Results after hydrolysis)

| Elapsed Time (min) | Yield of Citraconates (%) | Yield of CO2 (%) | Conversion of Succinates (%) | Selectivity[b] (%) |
|---|---|---|---|---|
| 60 | 34 | 10 | 56 | 61 |
| 150 | 22 | 6 | 54 | 41 |
| 180 | 25 | 4 | 35 | 71 |
| 270 | 20 | 4 | 44 | 46 |

[a]Reaction temperature = 380° C.; pressure = 60 psi; feed = 56 wt % DMS +15 wt % methanol + 24 wt % formaldehyde + 4 wt % water; liquid feed flow rate = 0.15 ml/min; molar ratio = 2 to 1 (formaldehyde to DMS)
[b]Selectivity of Citraconates = Yield of Citraconates * 100/(Conv of DMS − Yield of SA − Yield of MMS)

TABLE 9

Results from supports other than SA3177[a,b] (Results before hydrolysis)

| Run# | Supports | Yield of citraconic anhydride (%) | Conv of DMS (%) | Yield of CO2 (%) |
|---|---|---|---|---|
| 41[c] | Zeolite | 6 | 84 | 70 |
| 68 | Zirconia | 4 | 33 | 10 |
| 70 | SA6173 | 18 | 45 | 13 |
| 73 | Alumina (lab) | 18 | 56 | 18 |
| 77 | SA6175 | 16 | 71 | 30 |
| 80 | AlPO | 17 | 52 | 10 |

[a]Reaction temperature = 380° C.; pressure = 60 psi; feed = DMS + 1,3,5-trioxane (TO); liquid feed flow rate = 0.1 ml/min; molar ratio = 2/3 to 1 (TO to DMS).
[b]Results from a sample with maximum yield of citraconic anhydride is included here among several sample collected.
[c]Reaction temperature = 410° C.; pressure = 60 psi; feed = DES + 1,3,5-trioxane (TO); liquid feed flow rate = 0.1 ml/min; molar ratio = 2/3 to 1 (TO to DES); zeolite was impregnated with 5 mM cerium (IV) sulfate.

TABLE 10

1. Summary of results

| Run# | cat, support loading | Feed | Temp | Pres | Conv % | Yield % | C | Comments |
|---|---|---|---|---|---|---|---|---|
| 1 | CPG-3000 | DMS + TO(1:4) | 335–350 | 365 | — | — | = | Reactor outlet plugged after 3 samples, not much rxn |
| 2 | CPG-3000 | DMS | 330–370(20) | 300 | — | — | + | No rxn |
| 3 | 1 KH2PO4 CPG-3000 | DMS | 350–450(25) | 400 | | | | |
| 4 | 1 KH2PO4 CPG-3000 | DMS + TO(1:4.6) | 350–500(30) | 490 | 44. | 25(500) | + | First successful rxn, Two unknown peaks in HPLC |
| 5 | 1 KH2PO4 CPG-3000 | DMS + TO(1:4.6) | 400 | 290 | — | — | = | Reactor outlet plugged rightaway because of Trioxane |
| 6 | 1 KH2PO4 CPG-3000 | DMS + TO(1:4.6) | 400 | 290 | — | — | = | Reactor outlet plugged rightaway |
| 7 | 1 KH2PO4 CPG-3000 | DMS + TO(1:4) | 400–430 | 300 | 40 | .2(430) | = | Two samples collected, solid white stuff in tubing after sample trap |
| 8 | 1 KH2PO4 CPG-3000 | DMS | 400–500(25) | 480 | 49(500) | — | + | Losing some DMS at high temp |
| 9 | 1 KH2PO4 CPG-3000 | TO + Methanol | 350–500 | 490 | — | — | − | Losing 50% of feed, TO not analyzed |
| 10 | 1 KH2PO4 CPG-3000 | DES | 350–500(30) | 400 | 69(500) | — | + | |
| 11 | 2 KH2PO4 CPG-3000 | DES + TO(1:5) | 350 | 400 | — | — | = | Unsuccessful run, outlet blocked |
| 15 | CPG-3000 | — | 350–450(50) | 325 | — | — | = | No feed, only helium was flown through to see DMSO vaporization in trap |
| 16 | CPG-3000 | DES | 350–500(50) | 350 | 74(500) | — | = | Prod collected in DMSO |
| 17 | CPG-3000 | DES | 280–380(25) | 350 | 32(380) | — | = | |
| 18 | CPG-3000 | DES | 305–430(25) | 350 | 40(430) | — | = | Outlet gas was flown through liq N2 to trap CO2 or CO(nothing trapped) |
| 19 | 2 KH2PO4 CPG-3000 | DES + TO(1:4) | 350–470(30) | 370 | 55(470) | 0.8 | + | |
| 20 | 2 KH2PO4 CPG-3000 | DES + TO(1:4) | 350–440(30) | 375 | | | + | |
| 21 | 2 KH2PO4 CPG-500 | DES + TO(1:4) | 350–440(30) | 375 | | | + | |
| 22 | 2 KH2PO4 CPG-500 | DES + TO(1:4) | 350–440(30) | 375 | 70 | .8(440) | + | Try high surfacearea CPG next time |
| 23 | 2 KH2PO4 CPG-75 | DES + TO(1:4) | 350–410(30) | 375 | 48 | .4(440) | + | CPG is not good support, Bye CPG |
| 24 | 1 Li2CO3 SA3132 | DES + TO(1:4) | 350–440(30) | 375 | — | — | + | No conversion of DES and no CA yield |
| 25 | 1 Li2CO3 SA3132 | DES + TO(1:4) | 380 | 280 | — | — | + | No conversion of DES and no CA yield |
| 26 | .25 Ce3 Sulfate SA3132 | DES + TO(1:4.6) | 380 | 300 | 25 | 5.4 | + | products collected in DMSO |
| 27 | .25 Ce3 Sulfate SA3132 | DES + TO(1:1.5) | 380 | 300 | 42 | 4.5 | + | yield slightly decreased with decreasing molar ratio of feed |
| 28 | SA3132 | DES + TO(1:2) | 320–410(30) | 300 | 31 | 3.2(410) | + | Yield of CA increases with temp but also decreases with time |
| 29 | SA3132 | DES | 350–410(30) | 350 | 10 | — | − | Not much conversion of DES observed |
| 30 | SA3132 | DES + CA(4:1) | 350–410(30) | 350 | 20 | — | + | No conversion of CA @ low temp, but~30% conv @ 410 |
| 31 | 0.53 CeSulfate SA3132 | DES + TO(1:2) | 380–410(30) | 350 | 62(410) | 3.8 | − | Highest yield so far |
| 32 | 0.53 CeSulfate SA3132 | DES + TO(2:1) | 380–410(30) | 350 | 58 | 3.6(410) | − | Large unknown peak @21 in UV |
| 33 | 0.53 CeSulfate SA3132 | DES + TO(1:4) | 380–440(30) | 350 | 55 | 4.8(410) | − | high CO & CO2, low CA and bad mass balance at high temp |
| 34 | 0.39 CeSulfate SA3132 | DES + TO(1:2) | 380–410(30) | 60 | 50 | 5.6(380) | − | First rxn in new lab with new setup(eldex pump & valco valve in outlet), outlet clogged in beginning |
| 35 | 0.39 CeSulfate SA3132 | DES + TO(1:2) | 380–440(30) | 60 | 50 | 6.9(380) | = | large unknown peak @21 in UV, Feed treated with CaSO4 and cat calcined |
| 36 | 0.5 LaCl3 SA3132 | DES + TO(1:2) | 380–410(30) | 60 | 26 | 1(380) | = | Feed treated with CaSO4, high CO2 during first collection |
| 37 | 0.5 CeSulfate SA3132 | DES + TO(1:2) | 350–380(30) | 60 | — | — | − | short circuited heating tape could not collect samples |
| 38 | 0.5 CeSulfate SA3132 | DES + TO(1:2) | 410–470(30) | 60 | 50 | 7(410) | + | Unknown peak area decreased and MEC peak area increased after 5 days, large peak of DEC in esterified product |
| 39 | 0.5 CeSulfate SA3132 | DES + TO(2:1) | 410 | 60 | 52 | 7.8 | + | 15.5% yield on the basis of formaldehyde(limiting reactant), low CO2 |
| 40 | 0.5 CeSulfate SA3132 | DES | 410 | 60 | — | — | − | outlet was blocked by SA, could not collect sample nicely |
| 41 | 0.5 CeSulfate Zeolite-x | DES + TO(1:2) | 410 | 60 | 84 | 6.7 | + | Only water in first sample |
| 42 | 0.5 CeSulfate Zeolite-x | DES + TO(1:2) | 410 | 60 | — | — | + | to confirm water in first sample |
| 43 | 0.5 CeSulfate Zeolite-x | DES + TO(1:2) | 350 | 60 | — | — | + | rxn carried out at low temp to see activity of Zeolite, but lot of CO2 (>50%) |
| 44 | Zeolite-x | DES | 350 | 60 | — | — | + | More than 50% CO2 with only DES and only Zeolite, Zeolite too active |
| 45 | 2 KH2PO4 SA3132 | DES + TO(1:2) | 380 | 60 | 10 | 0.4 | + | KH2PO4 not suitable for this rxn |
| 46 | 0.5 CeSulfate SA3132 | DES + TO(1:2) | 380 | 60 | 53 | 7.8 | − | Rxn carried out to see reproducibility of results |
| 47 | 0.5 CeSulfate SA3132 | DES + form(1:3) | 380 | 60 | 50 | 5.2 | − | Two pumps to feed DES & formalin, feed preheated from now on |
| 48 | 0.5 CeSulfate SA3132 | DES + form(1:2) | 380 | 60 | 51 | 6.7 | = | Sod sulfite used to collect any formaldehyde (0.30%) in outlet |
| 49 | NdCl3 LaCl3 Zeolite-x | DES + form(1:2) | 380 | 60 | — | — | + | Ion exchanged cat, first sample water, second two phase, high CO2 |
| 50 | 0.5 CeSulfate Carbon | DES + form(1:2) | 380 | 60 | — | 0 | + | Activated carbon not active for this rxn |
| 51 | 0.5 CeSulfate SA3177 | DES + form(1:2) | 410 | 60 | 64 | 16.8 | + | MMC peak area increases with time |

TABLE 10-continued

1. Summary of results

| Run# | cat, support loading | Feed | Temp | Pres | Conv % | Yield % | C | Comments |
|---|---|---|---|---|---|---|---|---|
| 52 | 0.5 CeSulfate SA3177 | DES + form(1:2) | 410 | 60 | 87 | 17.2 | + | Same cat(R51) used after regeneration (flowing air at 410 C. for 6 hrs) |
| 53 | 0.5 CeSulfate SA3177 | DMS + form(1:1.3) | 410 | 60 | 75 | 22.5 | + | 7% yield of MMC, $CO_2$ decreases as product yield increases, High selectivity |
| 54 | 0.5 CeSulfate SA3177 | DMS + form(1:1.3) | 380 | 60 | 74 | 9.3 | + | yield of CA decreases with the temp |
| 55 | 0.75 CeSulfate SA3177 | DMS + form(1:1.3) | 380 | 60 | 87 | 12.2 | + | Yield increases with the loading |
| 56 | SA3177 | DMS + form(1:1.3) | 380 | 60 | 80 | 27 | + | 7.3% yield of MMC, low $CO_2$ |
| 57 | SA6175 | DMS + form(1:1.3) | 380 | 60 | — | — | = | Could not complete the experiment |
| 58 | SA6175 | DMS + form(1:1.3) | 380 | 60 | 92 | 15.5 | + | >50% $co_2$ observed and yield increases as conversion decreases with time. |
| 59 | SA6173 | DMS + form(1:1.3) | 380 | 60 | 94 | 15.3 | + | >50% $CO_2$ observed in a couple of collections. |
| 60 | 25:75::Al:Mg | DMS + form(1:1.3) | 380 | 60 | 83 | 0.65 | + | preferentially catalyses the cannizaro's reaction of form to MeOH |
| 61 | SA3177 | DMS + form(1:4) | 380 | 60 | 55 | 19.5 | + | Reactor temp accidentally want up 1200, prods analyzed only by R1, to confirm the yield |
| 62 | SA3177 | Formalin | 380 | 60 | — | — | + | 100% conversion of formaldehyde observed |
| 63 | SA3177 | Formalin | 380 | 60 | — | — | + | Previous experiment's result confirmed |
| 64 | SA3177 | DMS | 380 | 60 | 48 | — | + | |
| 65 | SA3177 | DMS + TO (1:2) | 380 | 60 | 49 | 20.5 | + | Yield goes up to 35% after hydrolysing the product, MMC & DMC confirmed |
| 66 | SA3177 | DMS + TO (1:2) | 410 | 60 | 89 | 14 | + | Yield decreases, conv increases, and $CO_2$ increases with temp |
| 67 | SA3177 | DMS + TO (1:2) | 350 | 60 | 33 | 16 | + | Low yield, but high selectivity |
| 68 | Zirconia | DMS + TO (1:2) | 380 | 60 | 33 | 3.7 | + | Zirconia is not sufficient active for the rxn |
| 69 | Fe2O3 | DMS + TO (1:2) | 380 | 60 | 35 | 0 | + | High yield of $CO_2$ with no CA |
| 70 | SA6173 | DMS + TO (1:2) | 380 | 60 | 45 | 18 | + | Lot of $CO_2$ in beginning, selectivity increases with time |
| 71 | SA3177 | DMS + TO (1:2) | 380 | 60 | 55 | 19 | + | Yield goes upto 30% after hydrolysing the product |
| 72 | TiO2 | DMS + TO (1:2) | 380 | 60 | 72 | 0 | + | No citraconates |
| 73 | Alumina(lab) | DMS + TO (1:2) | 380 | 60 | 56 | 18 | + | Alumina prepared in lab also gives similar results to alundum |
| 74 | SA6173 | DMS + TO (1:2) | 350 | 60 | — | — | + | Experiment could not completed |
| 75 | SA6173 | DMS + TO (1:2) | 350 | 60 | 36 | 15.5 | + | Low yield, but high selectivity |
| 76 | SA3177 | DMS + TO (1:2) | 380 | 400 | 53 | 20 | + | Low $CO_2$ observed, but same catalyst wt gain after the rxn |
| 77 | SA6175 | DMS + TO (1:2) | 380 | 60 | 71 | 16.3 | + | Lot of $CO_2$ in beginning, selectivity increases with time |
| 78 | SA3177 | DMS + TO (2:1) | 380 | 60 | 48 | 12 | + | 24% yield of CA based on formaldehyde |
| 79 | SA3177 | DMS + TO (1:2) | 380 | 400 | 50 | 18.5 | + | Run76 results confirmed, almost same results as at low P |
| 80 | AlPO | DMS + TO (1:2) | 380 | 60 | 52 | 17.3 | + | AlPO was prepared in lab, now AlPO can compete with Alndm |
| 81 | 85% ZrO2 + 15% Al2O3 | DMS + TO (1:2) | 380 | 60 | 34 | 6 | + | Run68(prprd in lab) results confirmed with this MieChem ZrO2 |
| 82 | TiO2 | DMS + TO (1:2) | 380 | 60 | 71 | 0 | + | Run72(prprd in lab) results confirmed with this Degusa titania |
| 83 | Fe2O3 | DMS + TO (1:2) | 380 | 60 | 40 | 0 | + | Run69(prprd in lab) results confirmed with this Aldrich Fe2O3 |
| 84 | 90:10:: Al : Mg | DMS + TO(1:2) | 380 | 60 | 80 | 1 | + | Nothing much different from high content of Mg(Run60) |
| 85 | 85% ZrO2 + 15% Al2O3 | DMS | 380 | 60 | 20 | — | + | No significant reaction with only DMS |
| 86 | glass beads | DMS | 380 | 60 | 0 | 0 | = | No reaction observed |
| 87 | KOH on SA3177 | DMS + TO(1:2) | 380 | 60 | 40 | 0 | + | 0.28 mmol KOH (more than acid sites) killed reaction completely |
| 88 | AlPO | DMS + TO(1:2) | 380 | 60 | 50 | 15 | + | AlPO prepared differently (from R80), but almost same result |
| 89 | K2CO3 on SA3177 | DMS + TO(1:2) | 380 | 60 | 70 | 0 | + | High conv in beginning, but decreasing sharply; no CA |
| 90 | Zeolite-x | DMS + TO(1:2) | 380 | 60 | 60 | 0 | + | Convs(93, 60, 26, 16, 11) % after 30 mins, NO CA |
| 91 | SA3177 | DMS + TO(1:2) | 380 | 60 | 43 | 32 | + | Extended run; results after hydrolysis, catalyst stable for 6 hrs |
| 92 | SA3177 | SAn + TO(1:5) | 380 | 60 | — | — | + | First rxn with SAN, pumped 30 ml in 20 min (pumps stupidity(not mine)) |
| 93 | SA3177 | SAn + TO(1:5) | 380 | 60 | 80 | 34 | + | First successful run with SAN, but with struggle; not bad yield |

TABLE 10-continued

1. Summary of results

| Run# | cat, support loading | Feed | Temp | Pres | Conv % | Yield % | C | Comments |
|---|---|---|---|---|---|---|---|---|
| 94 | SA3177 | SAn + TO(1:5) | 380 | 60 | 70 | 40 | + | Cat deactivates faster with SAN; Paraformaldehyde a problem |
| 95 | SA3177 | SAn + TO(1:2) | 380 | 60 | 75 | 43 | + | Not bad results, but cat dies soon and some other known problems |
| 96 | SA3177 | SAn + TO( 1:2) | 380 | 60 | 86 | 18 | + | Some leakage in feed, obviously high conv and low yield |
| 97 | SA3177 | SAn + TO(1:2) | 380 | 60 | 73 | 42 | + | Outlet gas flow rate increased 55 from 27 ml/min; 2 samples collected |
| 98 | SA3177 | SAn + TO(1:2) | 380 | 60 | 60 | 42 | + | Feed rate 10 from 6 ml/hr; 4 samples; nice results in beginning, but ... |
| 99 | SA3177 | SAn + TO(1:2) | 380 | 60 | — | — | + | High preheat 340 from ~200 C.; reaction stopped because of plugging |
| 100 | SA3177 | SAn + TO(1:2) | 380 | 60 | 68 | 33 | + | 6 samples, 12% yield in 6th sample |
| 101 | glass beads | SAn + TO(1:2) | 380 | 60 | 74 | 14 | + | Lot of CO2 ; no MMS; unreacted TO and formaldehyde |
| 102 | glass beads | SAn + TO(1:2) | 380 | 60 | 78 | 14 | + | Results from R101 confirmed |
| 103 | Empty Reactor | SAn + TO(1:2) | 380 | 60 | 0 | 0 | = | No reaction means it is not a thermal rxn |
| 104 | Fe2O3 | SAn + TO(1:2) | 380 | 60 | 100 | 0 | + | To see results from an inactive cat (our point of view) |
| 105 | Fe2O3 | SAn + TO(1:2) | 380 | 60 | 100 | 0 | + | Results from R104 confirmed |
| 106 | SA3177 | SAn + TO(1:2) | 350 | 80 | 37 | 30 | + | Very good results if we can reproduce; Yields(41, 30, 30 7, 19)% |
| 107 | SA3177 | SAn + TO(1:2) | 320 | 80 | 80 | 20 | + | Preheat here and R106 200 C.; At low rxn T feed cracks more bcos not vaporized |
| 108 | SA3177 | SAn + TO(1:2) | 350 | 80 | 60 | 30 | + | Outlet gas flow rate 82 from 55 ml/min; same yield, but more conv |
| 109 | SA3177 | SAn + TO(1:2) | 350 | 80 | 71 | 37 | + | Feed rate 6 from 10 ml/min; higher yield and higher conv |
| 110 | SA3177 | SAn + TO(1:2) | 350 | 80 | 85 | 20 | + | Feed rate 10 from 6 ml/hr; Gas rate 55 ml/min; Longer reactor but furnace not long |
| 113 | SA3177 | CAN | 350 | 80 | 24 | — | + | 80% of CAN recovered; no other products (only CO2 and CAN) |
| 114 | SA3177 | CAN | 350 | 80 | 30 | — | + | Product collection system new, but results same |
| 115 | SA3177 | CAN | 350 | 80 | 20 | — | + | He and top of the furnace not heated, but same results |
| 116 | SA3177 | SAn + TO(1:2) | 350 | 80 | 76 | 39 | + | Wanted to repeat R106, but high yield - high conv - low sel, 3 samples |
| 117 | SA3177 | MMS + methanol | 350 | 60 | 0 | — | + | Methanol as a solvent from now; no rxn here; no cat deactivation |
| 118 | SA3177 | MMS + TO (1:2) + me | 350 | 60 | 40 | 31 | + | Good sel; 32% DMS; Results after hydrolysis; low cat wt gain |
| 119 | SA3177 | MMS + TO (1:2) + me | 350 | — | 29 | 21 | + | No He; lot of DMS |
| 120 | SA3177 | MMS + TO(1:2) + me | 350 | — | 29 | 22 | + | No He; 45% DMS; good sel |
| 121 | SA3177 | MMS + TO(1:2) + me | 380 | 60 | 42 | 32 | + | Results almost same as at 350 C; |
| 122 | SA3177 | TO + methanol | 350 | 60 | 100 | — | + | Product gas only; I thought MTG process but Dr J says DME; ok he is right |
| 123 | SA3177 | methanol | 350 | 60 | 100 | — | + | Not much in the trap, No cannizaro here so only water in trap |
| 124 | 0.15 KH2PO4 SA3177 | MMS + TO(1:2)+me | 350 | 60 | 85 | 5 | + | Loading equivalent to acid sites, presence of base kills rxn |
| 125 | CPG-75 | MMS + TO(1:2) + me | 350 & 400 | 60 | 90 | 0 | + | No citraconates, but lot of DMS, No more CPGs from now |
| 126 | SA6175 | MMS + TO(1:2) + me | 350 | 60 | 30 | 18 | + | Results after hydrolysis; not great-similar to SA3177 |
| 127 | 98 Al + 2 Mg | DMS + Form (1:2) | 380 | 60 | 73 | 19 | + | Lot of CO2, lot of methanol, 25% CA & 42% conv after hydrolysis |
| 128 | SA3177 | DMS + Form (1:2) | 380 | 60 | 80 | 26 | + | Standard experiment, our optimal conditions |
| 129 | SA3177 | DMS + Form (1:2) | 380 | 60 | 77 | 26 | + | CO2 as a carrier; Same result as with helium as a carrier gas |
| 130 | 96 Al + 4 Mg | DMS + Form (1:2) | 380 | 60 | 73 | 17 | + | Hydrotalcites (HT) very reactive in beginning, bad MB in first 2–3 samples |
| 131 | 99 Al + 1 Mg | DMS + Form (1:2) | 380 | 60 | 75 | 20 | + | Increasing Mg in HT increases methanol |

TABLE 10-continued

1. Summary of results

| Run# | cat, support loading | Feed | Temp | Pres | Conv % | Yield % | C | Comments |
|---|---|---|---|---|---|---|---|---|
| 132 | 99.5 Al + 0.5 Mg | DMS + Form (1:2) | 380 | 60 | 89 | 23 | + | CA conversion increases with decreasing Mg in HT |
| 133 | Alumina(lab) | DMS + Form (1:2) | 380 | 60 | 81 | 23 | + | Increasing Mg in HT increases $CO_2$ also |
| 134 | Beads | DMS + Form (1:2) | 380 | 60 | 15 | 0 | + | Some MMS and SA in beginning, no CA like R101 & 102 |
| 135 | 0.015 KH2PO4 SA3177 | DMS + Form (1:2) | 380 | 60 | 81 | 26 | + | Loading equivalent to (acid sites/10), 33% CA at 43% conc after hydrolysis |
| 136 | 94 Al + 6 Mg | DMS + Form (1:2) | 380 | 60 | 63 | 17 | + | Conv of DMS decreases with increasing Mg in HT |
| 137 | 88 Al + 12 Mg | DMS + Form (1:2) | 380 | 60 | 61 | 12 | + | End of HT runs, see HT comparison tables |
| 138 | SA3177 | DMS + Form (1:2) | 380 | 60 | 76 | 24 | + | High He flow (double); FR = 0.23 ml/min; conv & Yield lower |
| 139 | SA3177 | DMS + Form (1:2) | 380 | 60 | — | — | + | Same as R140, but some human error |
| 140 | SA3177 | DMS + Form (1:2) | 380 | 60 | 74 | 21 | + | FR = 0.3 ml/min; increased preheat to 250 to vaporize feed complete |
| 141 | SA3177 | DMS + Formcel(1:2) | 380 | 60 | 81 | 35 | + | FR = 0.15 ml/min; bad MB because we lose MeOH in DME, good result |
| 142 | SA3177 | DMS + Formcel(1:2) | 380 | 60 | 66 | 22 | + | FR = 0.3 ml/min; conv & yield down; more cat wt gain than formalin |
| 143 | SA3177 | DMS + Formcel(1:2) | 380 | 60 | 65 | 20 | + | FR = 0.45 ml/min; didn't change much from above; |
| 144 | SA3177 | DMS + Formcel(1:2) | 380 | 60 | 59 | 9 | + | Same as R143, same cat, no regen; checked temp 3 diff points above reactor |
| 145 | SA3177 | DMS + Formcel(1:2) | 380 | 60 | — | — | + | |
| 146 | SA3177 | DMS + Formcel(1:4) | 380 | 60 | 66 | 26 | + | Inlet DMS molar fraction = 0.086 (const) in R146 to R149 |
| 147 | SA3177 | DMS + Form(1:2) | 380 | 60 | 62 | 21 | + | |
| 148 | SA3177 | DMS + Form(1:1) | 380 | 60 | 57 | 15 | + | Conversion decreases (not much) with decreasing formaldehyde |
| 149 | SA3177 | DMS + Form(1:0.5) | 380 | 60 | 52 | 10 | + | Yield decreases with decreasing formaldehyde |
| 150 | AlPO; P/Al = 1 | DMS + Form(1:2) | 380 | 60 | 81 | 20 | + | Not much methanol yield; high form conv; |
| 151 | AlPO; P/Al = 0.5 | DMS + Form(1:2) | 380 | 60 | 71 | 15 | + | High cat wt gain in those AlPO run compare to wt taken initially |
| 152 | AlPO; P/Al = 1.5 | DMS + Form(1:2) | 380 | 60 | 49 | 0 | + | No CA when P/Al = 1.5; Not much $CO_2$; not much form conv |
| 153 | SA3177 | DMS + Form(1:2) | 350 | 60 | 57 | 17 | + | Good sel at low temp, though low yield of CA |
| 154 | SA3177 | DMS + Form(1:2) | 350 | 60 | 72 | 19 | + | Longer Reactor; FR = 0.15 ml/min; not much diff from above |
| 155 | SA3177 | DMS + Form(1:2) | 350 | 60 | 65 | 14 | + | Longer Reactor; FR = 0.30 ml/min; follows R153 results |
| 156 | SA3177 | DMS + Form(1:2) | 350 | 60 | 62 | 15 | + | Same as R155; to see reproducibility=>excellent |
| 157 | SA3177 | Itaconic + water | 350 | 60 | 96 | 46 | + | IA converts into CA at rxn conditions, ~100% conv, very dil IA in feed |
| 158 | Empty Reactor | DMS + Form(1:2) | 350 | 60 | 0 | — | = | No loss of material; 100% recovery of form |
| 159 | SA3177 | DMS + Form(1:2) | 200 | 60 | 52 | — | + | Lot of $CO_2$, negligible CO; methanol 31% |
| 160 | AlPO | DMS + Form(1:2) | 200 | 60 | 61 | — | + | Not much $CO_2$, more CO, 28% methanol |
| 161 | SA3177 (acid treated) | DMS + Form(1:2) | 380 | 60 |  | 3 | + | High yield of SA, fresh cat blackish; |
| 162 | 66% Mg + 34% Al | DMS + Form(1:2) | 200 | 60 | 42 | — | + | Lot of $CO_2$, negligible CO; methanol 31% |
| 163 | SA3177 | DMS + Form(1:0.5) | 380 | 60 | 56 | 13 | + | High conv of form (see R164); not good sel |
| 164 | SA3177 | DMS + Form(1:0.5) | 380 | 60 | 61 | 13 | + | Cat regenerated from R163; cat activity preserves |

TABLE 10-continued

1. Summary of results

| Run# | cat, support loading | Feed | Temp | Pres | Conv % | Yield % | C | Comments |
|---|---|---|---|---|---|---|---|---|
| 165 | SA3178 | DMS + Form(1:2) | 380 | 60 | 74 | 22 | + | Mesh size 60/100; does not matter; not MT limited |

TO = Trioxane
form = formaldehyde
1 KH2PO4 CPG-3000 means 1 mmol loading of KH2PO4 on CPG3000
In DMS + TO (1:4), molar ratio is between DMS and Formaldehyde, not between DMS and Trioxane (TO)
In temperature cell, 350–500(30) means rxn is carried out in that temp range with 30 C. temp ramp
In conversion or yield cell, temp for best yield is given in bracket.
C means catalyst gain or loss,
+ means gain after the rxn.

Process Concept for Itaconic Acid Production from Succinates and Formaldehyde

Figure 6:
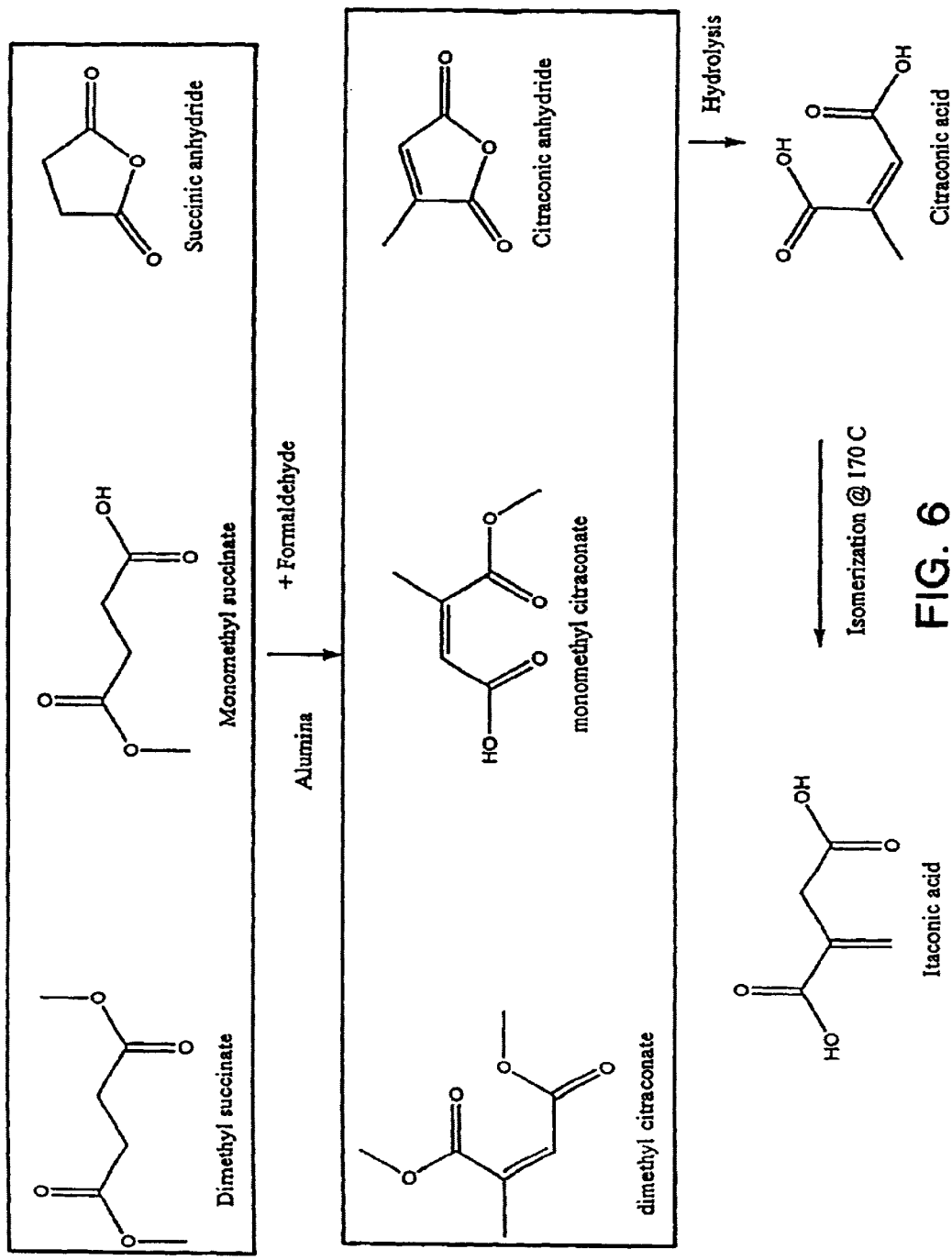
FIG. 6 is a diagram showing the reactions in the process of the present invention.
Figure 7:
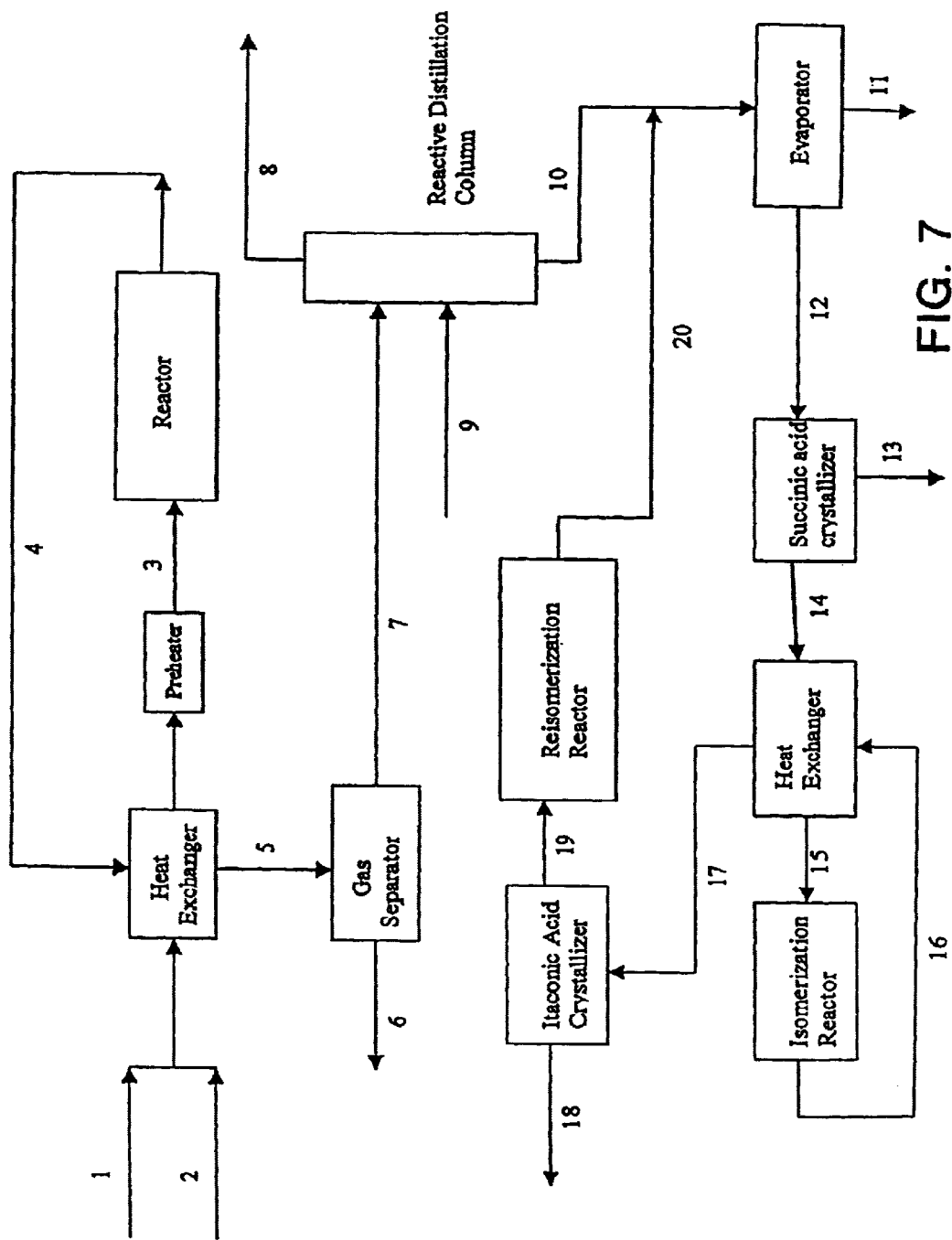
FIG. 7 is a schematic of a process for producing itaconate.

A schematic of the reactions involved in the process for conversion of succinate (SA) to itaconate (IA) via the Stobbe condensation is given in FIG. 6. As shown in FIG. 7, the primary components of the process are the reactor, where conversion takes place, a reactive distillation column where hydrolysis of succinates and citraconate takes place, and finally a crystallization/isomerization operation wherein succinate is crystallized out for recycle and citraconic acid (CA) is converted to itaconic acid.

At present, several catalysts and reagents have been identified from which itaconic acid can be formed. Reaction conditions have been optimized to maximize the yield and selectivity of the desired product. The catalyst deactivation and regeneration procedure have been characterized so that the catalyst can be used in a continuous process. It has been shown that citraconic anhydride can be converted to itaconic acid via catalytic isomerization and a process has been developed for the isomerization step.

The process implements a novel isomerization and crystallization recovery scheme that leads to higher yields of itaconic acid than in the prior art. The recovery scheme takes advantage of the high solubility of citraconic acid relative to succinic and itaconic acid, as well as the unexpected ability to recover nearly pure succinic acid or nearly pure itaconic acid from aqueous solutions containing high concentration of citraconic acid along with the acid to be recovered.

The key process steps involve succinate acid crystallization at low temperatures (10°–150° C.) following hydrolysis. Partial isomerization of citraconic to itaconic acid is then carried out, with conversion of citraconic acid limited to about 50–60% to avoid formation of unwanted byproducts. Itaconic acid is then crystallized out of solution at 20° to 250° C. and unreacted citraconic acid is recycled back into the process.

The preferred itaconate recovery steps of FIG. 7 involve first succinate crystallization at low temperatures (10–15° C.) following the hydrolysis via reactive distillation and water evaporation. The reheated liquor from the succinate crystallizaer is then passed to the isomerization reactor, where citraconic acid is converted at 140–200° C. to itaconic acid and byproducts citramalic acid and mesaconic acid. After cooling, itaconic acid is crystallized out of solution at 20–25° C. A higher temperature is used in itaconic acid crystallization than in succinate crystallization to avoid unwanted cocrystallization of residual succinic acid with itaconic acid. The liquor from itaconic acid crystallization is then passed through a reisomerization reactor at 200–300° C. to convert unrecovered itaconic acid and byproducts mesaconic acid and citramalic acid back to citraconic acid. Citraconic acid is then recycled back to the beginning of the recovery scheme.

Process Stream Description For FIG. 7

The numbers on FIG. 7 are:

1. Dimethyl succinate (DMS) or succinic anhydride feed;
2. Formaldehyde feed as Formalin, Formcell, trioxane, or gas-phase formaldehyde;
3. Combined heated feed to reactor: formaldehyde:succinate ratio is 0.5:1 to 5:1;
4. Reactor effluent: contains citraconates, unreacted succinates and formaldehyde, methanol, $CO_2$;
5. Cooled effluent stream;
6. Gases from reaction: mainly $CO_2$;
7. Liquid product effluent;
8. Overhead from reactive distillation column, containing methanol, formaldehyde, water. These species are recycled back to the beginning of the process;
9. Water feed for hydrolysis column;
10. Aqueous solution of citraconic acid, succinic acid;
11. Water vapor from evaporator;
12. Saturated solution of succinic acid at approx. 100° C. (also contains citraconic acid);
13. Succinic acid crystals;
14. Liquor from succinate crystallizer: T=10–15° C.; contains citraconic acid, succinic acid;
15. Heated liquor;
16. Effluent from isomerization reaction: contains primarily itaconic acid, plus unreacted citraconic acid, byproducts mesaconic acid and citramalic acid, and succinic acid;
17. Cooled isomerization reactor effluent;
18. Itaconic acid crystals;
19. Liquor from itaconic acid crystallization: contains itaconic acid, citraconic acid, succinic acid, citramalic acid, mesaconic acid. T=25° C.;
20. Effluent from reisomerization reactor: contains itaconic acid, succinic acid, citraconic acid. Recycled to upstream end of recovery system.

Itaconic acid and succinic acid can be recovered from mixed acid streams similar in composition to those expected in the process (as described in FIG. 7). Citraconic acid can be converted to itaconic acid at fairly high selectivity and yield in batch studies at 140–200° C. Mesaconic, citramalic, and itaconic acids can be converted back to citraconic acid at nearly 100% yield at 200–300° C.

The recovery scheme for separating citraconic acid from succinic acid and then converting citraconic acid to itaconic acid is shown in FIG. 7. The major steps in the process are the crystallization of succinic acid, the isomerization of citraconic acid to itaconic acid, crystallization of itaconic acid, and reisomerization of the byproducts of reaction back to citraconic acid. The reformed citraconic acid is recycled back to the feed point of the process, so that high overall yields of itaconic acid are achieved.

were dried, weighed, and then a portion was redissolved into solution and analyzed by HPLC for purity.

Results of succinate crystallization are shown in Table 11 below. Very high purity crystals of succinic acid are obtained from solution; crystallization at lower temperatures (13° C.) leads to a higher recovery of crystalline succinic acid from solution. Lower temperature crystallization is preferred in the process, both to enhance succinic acid recovery and to lower succinic acid concentration in the resulting liquor to a low enough value so that succinic acid does not co-crystallize with itaconic acid in the subsequent itaconic acid recovery step.

TABLE 11

Succinic Acid Crystallizations

| Crystallization Inputs | Crystallization temperature | Wash | Crystal composition | | | % SA crystallized |
|---|---|---|---|---|---|---|
| | | | % CA | % SA | % IA | |
| 8.49 g CA, 7.8 g SA, .448 g IA, 10.00 g H$_2$O | 22° C. | 35 g cold water | 0.14 | 99.69 | 0.17 | 58.55 |
| 8.50 g CA, 7.09 g SA, .44 g IA, 10.01 g H$_2$O | 13° C. | 40 g cold water | 0.20 | 99.80 | 0.00 | 69.96 |
| 23.62 g CA, 7.08 g SA, 1.12 g IA, 10.024 g H$_2$O | 22° C. | 27 g cold water | 0.30 | 99.34 | 0.36 | 60.83 |

The recovery scheme integrates all of the steps along with succinate removal to achieve an efficiency of conversion of citraconic acid to itaconic acid higher than that reported heretofore in the literature.

The following examples describe experiments demonstrating the various steps of the recovery scheme. The compositions of the starting materials in each example have been chosen to simulate the stream compositions in the recovery scheme shown in FIG. 7.

Succinic Acid Crystallization

Crystallization of succinic acid from an aqueous solution of mixed acids was carried out in the laboratory. The predetermined amounts of citraconic, succinic, and itaconic acids and water (Table 11 below) were weighed out and combined in a flask with a magnetic stir bar. The mixture was then heated, under reflux, in a constant temperature water bath to 85° C. with stirring. When all solid materials had entered into solution, the flask was removed from the water bath and either allowed to cool to room temperature (22° C.) or cooled using a cold water bath to 13° C. After cooling the crystals were vacuum filtered and washed with water that had been chilled in an ice-water bath. The crystals were then collected and either air dried or dried at 50° C. The residual liquor and the wash solution were analyzed by high performance liquid chromatography (HPLC). The crystals Itaconic Acid Crystallization Predetermined amounts of citraconic, succinic, and itaconic acids and water were weighed out and combined in a flask with a magnetic stir bar. The mixture was then heated, under reflux, in a constant temperature water bath to 95° C. with stirring. When all solid materials had entered into solution the flask was removed from the water bath and allowed to cool to room temperature (22° C.). After cooling the crystals were vacuum filtered and washed with water that had been chilled in an ice-water bath or a room temperature saturated solution of itaconic acid. The crystals were then collected and either air dried or dried at 50° C. The solution of the liquor and washings was analyzed by HPLC; the crystals formed were dried, weighed and then redissolved in water to identify any impurities present in the product.

Results from several crystallization experiments are given in Table 12. Very high purity itaconic acid crystals are obtained. Recovery is enhanced by washing crystals in a saturated solution of itaconic acid in water. To further improve the purity of itaconic acid formed, the crystals formed as reported above were further purified by recrystallization in ethanol. The recrystallization in ethanol gave itaconic acid in a purity exceeding 99.5%.

TABLE 12

Itaconic Acid Crystallizations

| Crystallization Inputs | Wash | Crystal composition | | | % IA crystallized |
|---|---|---|---|---|---|
| | | % CA | % SA | % IA | |
| 8.01 g CA, 0.81 g SA, 13.06 g IA, 10.00 g H$_2$O | 70 g cold water | 0.01 | 1.34 | 98.65 | 55.13 |
| 8.07 g CA, 0.41 g SA, 13.04 g IA, 10.006 g H$_2$O | 26 g cold water | 0.09 | 0.70 | 99.21 | 72.07 |
| 9.201 g CA, 0.937 g SA, 15.08 g IA, 11.588 g H$_2$O | 55 g room temp. sat. IA solution | 0.14 | 1.46 | 98.40 | 80.78 |

Isomerization of Citraconic Acid to Itaconic Acid

Isomerization was done in a 300 mL stirred autoclave reactor (Parr Instrument Co., Joliet, Ill.). The reactor was charged with desired quantities of citraconic acid and water to total of approximately 100 ml volume; in selected experiments acid (0.005 M H$_2$SO$_4$) or base (NH$_4$OH) was also added to examine the effect of pH on reaction. Solutions were heated to desired temperature and maintained there with agitation. Samples of the reaction solution were taken during reaction and analyzed in HPLC.

Results of isomerization experiments are given in Table 13. Yields of itaconic acid fed above 60% are achieved, with selectivity (mole itaconic acid formed/mole citraconic acid converted) approaching 90% in some reactions. There exists an optimum reaction time (for example, 3 hours @ 170° C.); longer reaction times lead to conversion of itaconic acid to undesired byproducts. Adding acid to lower pH does not markedly enhance itaconic acid yield; addition of base (not shown) reduced itaconic acid yield and was not pursued. The reaction can therefore be considered purely a thermal reaction, requiring no catalyst addition to the citraconic acid solution in order to achieve good yields and selectivities to itaconic acid.

Reisomerization of Citramalic, Mesaconic, and Itaconic Acid to Citraconic Acid

The by product acids citramalic acid and mesaconic acid formed in the isomerization step are recovered by converting them back to citraconic acid at elevated temperature over the same alumina (Norton SA3177) used as the catalyst for citraconic acid formation from formaldehyde and succinate. The itaconic acid remaining in the liquor following the itaconic acid crystallization step is also converted back to citraconic acid at these conditions. Two examples are provided below.

Conversion of Citramalic Acid to Citraconic Acid

A solution of 22 wt % citramalic acid in water was fed to the flow reactor described previously for converting dimethyl succinate and formaldehyde to citraconic acid. The reactor contained 5 g of Norton SA3177 Alundum (alumina) at a temperature of 270° C. The solution feed rate was 0.5 ml/min and the accompanying helium carrier flow rate was 55 ml/min, giving a weight hourly space velocity (WHSV) of 1.3 kg citramalic acid/kg alumina/hr. Only citraconic acid was detected in the liquid product solution; no citramalic acid or other products were observed. This indicates that the conversion of citramalic acid to citraconic anhydride is complete at these conditions.

Recovery Process

Here the sequential isomerization of citraconic acid to itaconic acid, crystallization of itaconic acid, and reisomerization of byproducts back to citraconic acid are demonstrated. Citraconic acid (60 g) was dissolved in 120 g water and placed in a batch autoclave reactor. The reactor was heated to 170° C. and stirred for 3 hours, then cooled. The resulting slurry was then filtered to recover 28 g of itaconic acid crystals that formed during the cooling (crystallization) step (yield is 47% of theoretical) The residual liquor was analyzed by HPLC and found to contain itaconic acid, citramalic acid, mesaconic acid, and citraconic acid. This liquor was passed over 5 g Norton SA3177 alumina in the flow reactor at 270° C. and 20 psig pressure. The liquor feed rate was 0.5 ml/min and the accompanying helium flow rate was 150 ml/min, to give a WHSV of 1.2 kg combined acids/kg alumina/hr. Analysis by HPLC revealed of the liquid effluent from the reactor showed that the only compounds present were citraconic acid and itaconic acid. Thus complete conversion of citramalic and mesaconic acid byproducts and partial conversion of uncrystallized itaconic acid was achieved. The quantity of citraconic acid in the effluent was 24.7 g along with 2.7 g itaconic acid. Thus, the final yield of itaconic acid was 30.7 g from 35.3 g citraconic acid converted, or 87% of theoretical.

TABLE 13

Isomerization of Citraconic Acid (CA)

| Feed Composition | Reaction Temperature (° C.) | Reaction time (hr) | Citraconic acid conversion | Yields (% theoretical) | | |
|---|---|---|---|---|---|---|
| | | | | Itaconic acid | Mesaconic acid | Citramalic acid |
| 13 g CA 117 g H$_2$O | 170 | 3 | 69.8 | 61.1 | 0 | 9.0 |
| 13 g CA 117 g H$_2$O | 170 | 10 | 88.3 | 53.0 | 3.5 | 17.6 |
| 10 g CA 90 g H$_2$O | 190 | 1 | 72.3 | 62.9 | 0 | 10.4 |

TABLE 13-continued

Isomerization of Citraconic Acid (CA)

| Feed Composition | Temperature (° C.) | Reaction time (hr) | Citraconic acid conversion | Yields (% theoretical) | | |
|---|---|---|---|---|---|---|
| | | | | Itaconic acid | Mesaconic acid | Citramalic acid |
| 10 g CA 90 g H$_2$O | 190 | 3 | 86.2 | 56.8 | 4.1 | 15.6 |
| 10 g CA 90 g H$_2$O | 150 | 3 | 20.6 | 25.0 | 0 | N/A |
| 50 g CA 50 g H$_2$O | 170 | 3 | 79.8 | 55.1 | 1.1 | 6.9 |
| 10 g CA 90 g H$_2$O 0.005 M H$_2$SO$_4$ | 170 | 3 | 73.0 | 62.4 | 0 | 10.6 |
| 10 g CA 90 g H$_2$O 0.005 M H$_2$SO$_4$ | 170 | 3 | 68.4 | 57.9 | 0 | 9.5 |

Improved Process Incorporating Generation of Formaldehyde in the Process

Figure 10:
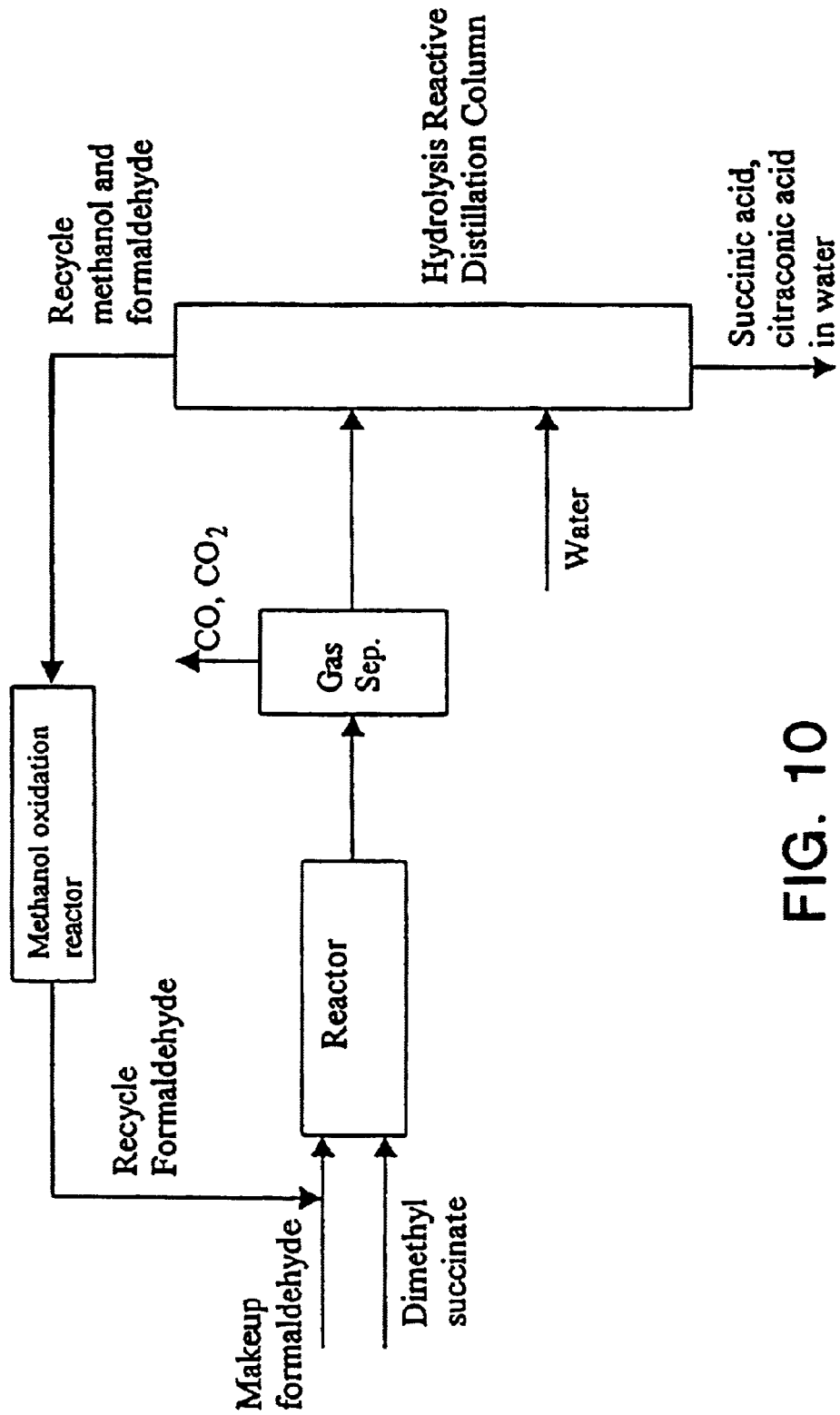
FIG. 10 is a schematic diagram showing an improved scheme for producing formaldehyde.

This improvement shown in FIG. 10 is based on producing formaldehyde in its pure gaseous form via catalytic oxidation of methanol generated in the reactor. Production of formaldehyde from methanol represents a savings in raw material and shipping costs, as formaldehyde generated off-site (at $0.09 per lb 37% solution) is substantially more expensive than methanol ($0.11/lb in pure form). More importantly, this scheme eliminates the potential problems in separating methanol and formaldehyde when the reaction process is run in an excess of formaldehyde. As methanol is liberated from dimethyl succinate, it passes out the top of the hydrolysis column along with a mixture of water and unreacted formaldehyde. Depending on the formaldehyde conversion and molar ratio, the entire stream can be passed through an oxidation reactor to make a stream of formaldehyde for the reaction. The purity requirements on the stream are minimal, so complete conversion of methanol is not necessary because there is methanol in the reactor anyway.

The patent literature describes several methods for the catalytic oxidation of methanol to formaldehyde. The process is commonly practiced commercially using either silver or molybdenum-based catalysts. The reactant is typically an aqueous solution of methanol, although mixtures of methanol, water, and formaldehyde are also used. U.S. Pat. Nos. 4,967,014; 4,450,301; 4,420,641; and 3,987,107 all describe conversion of methanol/water solution to formaldehyde solution over silver catalysts. In some cases two reactors in series are used to enhance overall conversion and yield; conversion of methanol to formaldehyde in excess of 90% is reported in these patents.

This step improves the overall process economics of itaconic acid formation. The quantity of water in the overhead stream of the reactive distillation is controllable by controlling the temperature and reflux ratio of the column.

The process does not have to include all operations in FIG. 7 in order to be covered under this application. For instance, the reisomerization reactor or the methanol oxidation to formaldehyde do not have to be included in order for the process to be viable. Further, the separation and hydrolysis do not have to be in a reactive distillation column in order for the process to be viable.

It is intended that the foregoing description be only illustrative of the present invention and that the present invention be limited only by the hereinafter appended claims.

We claim:

1. A process for the preparation of citraconic anhydride which comprises: contacting a molar excess of an aqueous solution of formaldehyde, gaseous formaldehyde or trioxane in a solvent with at least one compound selected from the group consisting of succinic anhydride, mono- and di-lower alkyl esters of succinic acid in vapor phase with a metal oxide catalyst at a temperature from about 320° to 440° C., at a pressure from about 20 to 400 psi, at a Weight Hourly Space Velocity (WHSV) from about 0.3 to 4 kg succinate/hr*kg catalyst, the catalyst consisting of a porous material having a surface area between about 30 m$^2$/g and 700 m$^2$/g, surface acid site density from about 66 to 2350 micromole/g, surface base site density from about 0 to 500 micromole/g and acid strength (pKa) of about +3 to −3 until reaction is substantially complete and recovering from the reaction products the citraconic anhydride thereby produced, said lower alkyl having from 1 to 4 carbon atoms.

2. The process of claim 1 wherein the porous material is gamma-alumina, which is prepared by a process which comprises: reacting aluminum chloride and ammonia in an aqueous solution with stirring for a period of at least 3 hours to form a precipitate, aging the precipitate for at least 12 hours, separating the precipitate, drying the precipitate, for at least about 12 hours and calcining the precipitate at above about 500° C. for at least about 3 hours.

3. The method of claim 1 wherein the porous material is titanium oxide, which is prepared by a process which comprises: reacting the acidic aqueous solution of titanium (IV) butoxide and ammonia with stirring for a period of at least 3 hours to form a precipitate, aging the precipitate for at least 12 hours, separating the precipitate, drying the precipitate, for at least about 12 hours, and calcining the precipitate at above 400° C. for at least 3 hours.

4. The process of claim 1 wherein the porous material is one of a series of Mg—Al mixed oxides with Mg/(Mg+Al) ratios of 0.005, to 0.75 to 1, which is prepared by a process which comprises: reacting aluminum nitrate, magnesium, chloride, and ammonia in an aqueous solution with stirring for a period of hours to form a precipitate, aging the precipitate for at least about 12 hours, separating the precipitate and drying the precipitate.

5. The process of claim 1 wherein the porous material is one of a series of aluminum phosphates with P/Al ratios of 0.5 to 1.5 to 1, which is prepared by a process which comprises: reacting aluminum nitrate, ammonium hydrogen phosphate, and ammonia in an acidic aqueous solution with stirring for a period of hours to form a precipitate, aging the precipitate for at least about 12 hours, separating the precipitate and drying the precipitate.

6. The process of claim 1 wherein the porous material is gamma-alumina impregnated with potassium hydroxide or sodium hydroxide.

7. The method of claim 1 wherein the porous material is gamma-alumina which is regenerated to remove carbon after the process, by passing air over a deactivated gamma-alumina catalyst at 500° C. so that carbon dioxide is evolved from the carbon until the carbon is removed.

* * * * *

UNITED STATES PATENT AND TRADEMARK OFFICE
CERTIFICATE OF CORRECTION

PATENT NO. : 6,649,774 B2  Page 1 of 1
APPLICATION NO. : 10/226474
DATED : November 18, 2003
INVENTOR(S) : Dennis J. Miller et al.

It is certified that error appears in the above-identified patent and that said Letters Patent is hereby corrected as shown below:

Column 3, line 61, "4,235,756 to Slauqh;" should be --4,235,756 to Slaugh;--.

Column 4, line 36, "three forms Initially," should be --three forms. Initially,--.

Column 5, line 32, "coca talyts:" should be --cocatalysts:--.

Column 6, line 25, "nonahydrate" should be --nonanhydrate--.

Columns 15 and 16, Table 10, run 4, "44." should be --44--.

Columns 15 and 16, Table 10, run 4, "25 (500)" should be --.25 (500)--.

Column 17, run 90, "380" should be --300--.

Column 23, line 49, "(10°-150° C.) should be --(10°-15°C)--.

Column 23, line 54, "250°C." should be --25°C--.

Column 23, line 60, "crystallizaer" should be --crystallizer--.

Column 26, Table 11, line 1 of Table, "8.49 g CA, 7.8 g SA," should be --8.49g CA, 7.08g SA,--.

Signed and Sealed this

Eighth Day of January, 2008

JON W. DUDAS
*Director of the United States Patent and Trademark Office*